(12) United States Patent
Varga et al.

(10) Patent No.: US 9,999,552 B2
(45) Date of Patent: Jun. 19, 2018

(54) METHODS FOR PROFILING SURFACE TOPOGRAPHIES OF ABSORBENT STRUCTURES IN ABSORBENT ARTICLES

(71) Applicant: The Procter & Gamble Company, Cincinnati, OH (US)

(72) Inventors: Stephen Michael Varga, Loveland, OH (US); Walter Pieter Hendrik Laurentius Van der Klugt, Mechernich Satzvey (DE); Rene Gaber, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 477 days.

(21) Appl. No.: 14/629,762

(22) Filed: Feb. 24, 2015

(65) Prior Publication Data

US 2015/0245954 A1 Sep. 3, 2015

Related U.S. Application Data

(60) Provisional application No. 61/945,893, filed on Feb. 28, 2014.

(51) Int. Cl.
*A61F 13/15* (2006.01)
*B32B 37/24* (2006.01)
(Continued)

(52) U.S. Cl.
CPC .. *A61F 13/15772* (2013.01); *A61F 13/15634* (2013.01); *A61F 13/15658* (2013.01);
(Continued)

(58) Field of Classification Search
CPC .......... A61F 13/15634; A61F 13/15658; A61F 13/15699; A61F 13/15723;
(Continued)

(56) References Cited

U.S. PATENT DOCUMENTS 3,860,003 A 1/1975 Buell
4,610,678 A 9/1986 Weisman et al.
(Continued)

FOREIGN PATENT DOCUMENTS

EP 0 149 880 A2 5/1985
EP 1 528 907 B1 9/2008
(Continued)

OTHER PUBLICATIONS

PCT/US2015/017426 International Search Report, dated May 27, 2015, 13 pages.

*Primary Examiner* — George Koch
(74) *Attorney, Agent, or Firm* — Charles R. Matson

(57) ABSTRACT

The present disclosure relates to methods and apparatuses for sensing distortions in patterns of reflected light to create profiles representing surface topographies of absorbent structures during the manufacture of absorbent articles. Inspection systems may include sensors arranged adjacent an advancing absorbent structure on a converting line. In turn, a controller may monitor and affect various operations on the converting line. The inspection systems herein may also include a radiation source that illuminates a surface of an absorbent structure with a predetermined pattern of light extending in the cross direction CD. The sensor senses distortions in patterns of light reflected from the illuminated surface of the absorbent structure and triangulates changes in elevation of the illuminated surface of the absorbent structure relative to the sensor. Based on the triangulated changes in elevation, the sensor creates a profile representing a surface topography of the illuminated surface of the absorbent structure.

24 Claims, 16 Drawing Sheets

(51) Int. Cl.
  *B05D 5/00* (2006.01)
  *B32B 37/00* (2006.01)
  *B32B 38/06* (2006.01)
  *B32B 41/00* (2006.01)

(52) U.S. Cl.
  CPC .. *A61F 13/15699* (2013.01); *A61F 13/15723* (2013.01); *A61F 13/15731* (2013.01); *B05D 5/00* (2013.01); *B32B 37/0076* (2013.01); *B32B 37/24* (2013.01); *B32B 38/06* (2013.01); *B32B 41/00* (2013.01); *A61F 2013/15821* (2013.01); *B32B 2037/243* (2013.01); *B32B 2307/726* (2013.01); *B32B 2535/00* (2013.01)

(58) Field of Classification Search
  CPC ...... A61F 13/15731; A61F 2013/15788; A61F 2013/15796; A61F 2013/15821; B05D 5/00; B32B 37/0076; B32B 37/24; B32B 38/06; B32B 41/00; B32B 2037/243; B32B 2307/726
  USPC .......................................................... 156/64
  See application file for complete search history.

(56) References Cited

U.S. PATENT DOCUMENTS

| | | | |
|---|---|---|---|
| 4,834,735 A | 5/1989 | Alemany et al. | |
| 4,888,231 A | 12/1989 | Angstadt | |
| 4,919,738 A | 4/1990 | Ball et al. | |
| 4,940,464 A | 7/1990 | Van Gompel et al. | |
| 5,037,416 A | 8/1991 | Allen et al. | |
| 5,092,861 A | 3/1992 | Nomura et al. | |
| 5,137,537 A | 8/1992 | Herron et al. | |
| 5,151,092 A | 9/1992 | Buell et al. | |
| 5,246,433 A | 9/1993 | Hasse et al. | |
| 5,260,345 A | 11/1993 | DesMarais et al. | |
| 5,269,775 A | 12/1993 | Freeland et al. | |
| 5,286,543 A | 2/1994 | Ungpiyakul et al. | |
| 5,359,525 A | 10/1994 | Weyenberg | |
| 5,387,207 A | 2/1995 | Dyer et al. | |
| 5,397,316 A | 3/1995 | LaVon et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,702,551 A | 12/1997 | Huber et al. | |
| 5,897,545 A | 4/1999 | Kline et al. | |
| 5,957,908 A | 9/1999 | Kline et al. | |
| 6,004,306 A | 12/1999 | Robles et al. | |
| 6,120,487 A | 9/2000 | Ashton | |
| 6,120,489 A | 9/2000 | Johnson et al. | |
| 6,248,195 B1 | 6/2001 | Schmitz | |
| 6,563,013 B1 | 5/2003 | Murota | |
| 6,620,144 B1 * | 9/2003 | Glasgow | A61F 13/47227 604/385.01 |
| 6,620,276 B1 | 9/2003 | Kuntze et al. | |
| 6,645,569 B2 | 11/2003 | Cramer et al. | |
| 6,801,828 B2 | 10/2004 | Popp et al. | |
| 6,811,019 B2 | 11/2004 | Christian et al. | |
| 6,820,022 B2 | 11/2004 | Popp et al. | |
| 6,863,933 B2 | 3/2005 | Cramer et al. | |
| 7,108,759 B2 | 9/2006 | You et al. | |
| 7,112,621 B2 | 9/2006 | Rohrbaugh et al. | |
| 7,123,981 B2 | 10/2006 | Dollevoet et al. | |
| 7,460,250 B2 | 12/2008 | Keightley et al. | |
| 7,489,410 B2 | 2/2009 | Nishio | |
| 7,587,966 B2 | 9/2009 | Nakakado et al. | |
| 7,667,857 B2 | 2/2010 | Nishio | |
| 8,145,343 B2 | 3/2012 | DeBruler et al. | |
| 8,145,344 B2 | 3/2012 | DeBruler et al. | |
| 8,244,393 B2 | 8/2012 | McLaughlin et al. | |
| 8,568,566 B2 | 10/2013 | Jackels et al. | |
| 8,603,277 B2 | 12/2013 | Paldey et al. | |
| 8,658,852 B2 | 2/2014 | Paldey | |
| 2003/0105190 A1 | 6/2003 | Diehl et al. | |
| 2003/0148684 A1 | 8/2003 | Cramer et al. | |
| 2003/0233082 A1 | 12/2003 | Kline et al. | |
| 2004/0158212 A1 | 8/2004 | Ponomarenko et al. | |
| 2005/0008839 A1 | 1/2005 | Cramer et al. | |
| 2005/0111009 A1 | 5/2005 | Keightley et al. | |
| 2005/159720 A1 | 7/2005 | Gentilcore et al. | |
| 2006/0116653 A1 | 6/2006 | Munakata et al. | |
| 2008/0031621 A1 | 2/2008 | Kuo et al. | |
| 2010/0036349 A1 * | 2/2010 | Hammons | A61F 13/51305 604/385.01 |
| 2010/0051166 A1 * | 3/2010 | Hundorf | A61F 13/15658 156/62.8 |
| 2012/0316046 A1 | 12/2012 | Jackels et al. | |
| 2013/0213547 A1 | 8/2013 | Schneider et al. | |
| 2013/0218116 A1 | 8/2013 | Schneider et al. | |
| 2014/0110053 A1 | 4/2014 | Ordway et al. | |
| 2014/0163504 A1 | 6/2014 | Bianchi et al. | |
| 2014/0377506 A1 | 12/2014 | Eckstein et al. | |
| 2014/0377513 A1 | 12/2014 | Galie et al. | |

FOREIGN PATENT DOCUMENTS

| | | | |
|---|---|---|---|
| WO | WO 1995/016746 | 6/1995 | |
| WO | WO 2002/064877 | 8/2002 | |
| WO | WO 2008143560 A1 * | 11/2008 | ....... A61F 13/49012 |
| WO | WO 2010/141547 A1 | 9/2010 | |
| WO | WO 2012/125537 A1 | 9/2012 | |
| WO | WO 2012/170781 A1 | 12/2012 | |
| WO | WO 2013/031143 A1 | 3/2013 | |

* cited by examiner

METHODS FOR PROFILING SURFACE TOPOGRAPHIES OF ABSORBENT STRUCTURES IN ABSORBENT ARTICLES

CROSS REFERENCE TO RELATED APPLICATION

This application claims the benefit of U.S. Provisional Application No. 61/945,893 filed on Feb. 28, 2014, which is incorporated herein by reference.

FIELD OF THE INVENTION

The present disclosure relates to methods and apparatuses for making absorbent articles with absorbent structures, and more particularly, sensing distortions in patterns of reflected light to create profiles representing surface topographies of absorbent structures during the manufacture of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, acquisition layers, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

In some configurations, absorbent articles may include absorbent structures positioned between the topsheets and backsheets. In addition, absorbent structures may include acquisition layers and absorbent cores, wherein the acquisition layers may be positioned between the absorbent cores and topsheets. As such, the topsheets, backsheets, and absorbent structures of such absorbent articles may function to absorb and/or contain the discharged materials and also to isolate bodily exudates from the wearer's skin and from the wearer's garments and bed clothing. For quality control purposes, absorbent article manufacturing lines may utilize various types of sensor technology to detect various types of characteristics of webs and discrete components added to the webs along the converting line as absorbent articles are constructed. Example sensor technology may include vision systems, photoelectric sensors, proximity sensors, laser or sonic distance detectors, and the like. In turn, sensor data may be communicated to a controller in various ways. In some configurations, the controller may be programmed to utilize sensor data to make operational adjustments; communicate converting line operating information; and/or reject defective diapers.

Although the previously mentioned sensor technology may be configured to provide information about the presence or absence of various components as well as relative positions and/or perimeter shapes of such components, such sensor technology may not be configured to provide desired information about absorbent structures. Absorbent structures may be constructed in various ways in an attempt to improve wearer fit and comfort and/or the manner in which absorbent structures absorb and/or transport liquid discharged onto and through a topsheet. For example, the absorbent structures may be constructed in various shapes and/or with varying amounts of absorbent material arranged along a width and/or length. In some instances, absorbent cores may be constructed with regions having no absorbent material or relatively small amounts of absorbent material. Such regions may provide improved core bending flexibility in use. In addition, some acquisition layers may be constructed with varying thicknesses along the length and/or width. For example, some absorbent structures may be configured with acquisition layers having relatively thicker regions located within absorbent articles in positions relatively near where discharges of liquid from a wearer is relatively more likely to occur. In efforts to improve and control quality of manufactured absorbent articles, it may be desirable to obtain additional detailed information about the construction of such absorbent cores and/or acquisition layers during the assembly process. Consequently, it would be beneficial to obtain information about the surface topography and/or thicknesses of absorbent cores and/or acquisition layers during the assembly process.

SUMMARY OF THE INVENTION

The present disclosure relates to methods and apparatuses for sensing distortions in patterns of reflected light to create profiles representing surface topographies of absorbent structures during the manufacture of absorbent articles. Aspects of the present disclosure relate to the fabrication of absorbent articles wherein an inspection system may be configured to interact with, monitor, and/or control a converting line. The inspection system may include sensors arranged adjacent an advancing absorbent structure on a converting line and may communicate with a controller. In turn, the controller may monitor and affect various operations on the converting line. The inspection systems herein may also include a radiation source that illuminates a surface of an absorbent structure with a predetermined pattern of light extending in the cross direction CD. The sensor senses distortions in patterns of light reflected from the illuminated surface of the absorbent structure and triangulates changes in elevation of the illuminated surface of the absorbent structure relative to the sensor. Based on the triangulated changes in elevation, the sensor creates a profile representing a surface topography of the illuminated surface of the absorbent structure.

In one form, a method for assembling disposable absorbent articles, wherein each absorbent article includes a topsheet, a backsheet, and a substantially cellulose free absorbent core disposed between the topsheet and the backsheet, includes the steps of: advancing a first continuous substrate in a machine direction, the first continuous substrate having a first surface and an opposing second surface, and defining a width in a cross direction; depositing absorbent particulate polymer material on the first surface of the first continuous substrate so as to define first regions of absorbent particulate polymer material surrounding second regions that are substantially free of absorbent particulate polymer material; advancing a second continuous substrate in the machine direction, the second continuous substrate having a first surface and an opposing second surface, and defining a width in the cross direction; depositing absorbent particulate polymer material on the first surface of the second continuous substrate so as to define first regions of absorbent particulate polymer material surrounding second regions that are substantially free of absorbent particulate polymer material; combining the first continuous substrate with the second continuous substrate to create a continuous length of substantially cellulose free absorbent cores, wherein the second regions on the first continuous substrate and the second continuous substrate are placed in facing relationships to define channel regions having a first thickness T1 surrounded by absorbent particulate polymer material areas having a second thickness T2, wherein first thickness T1 is less than the second thickness T2; advancing the continuous length of substantially cellulose free absorbent cores past a sensor such that the second continuous substrate is between the sensor and the first continuous substrate; illuminating the second surface of the second continuous substrate of the continuous length of substantially cellulose free absorbent cores with a predetermined pattern of light extending in the cross direction; sensing distortions in patterns of the light reflected from the second surface of the second continuous substrate with the sensor to triangulate changes in elevation of the second surface of the second continuous substrate relative to the sensor; and creating a profile representing a surface topography of channel regions in the continuous length of substantially cellulose free absorbent cores from the triangulated changes in elevation.

In another form, a method for assembling disposable absorbent articles, wherein each absorbent article includes a topsheet, a backsheet, and a liquid acquisition layer and an absorbent core disposed between the topsheet and the backsheet, includes the steps of: advancing a continuous length of a first acquisition layer substrate in a machine direction the first continuous length of the first acquisition layer substrate having a first surface and an opposing second surface, and defining a width in a cross direction; depositing discrete patches of second acquisition layers on the continuous length of the first acquisition layer substrate, wherein each discrete patch includes a first surface and an opposing second surface, wherein the second surface of each discrete patch is in a facing relationship with the first surface of the continuous length of the first acquisition layer substrate; advancing the continuous length of the first acquisition layer substrate past a sensor such that discrete patches of second acquisition layers advance between the sensor and the continuous length of the first acquisition layer substrate; illuminating the first surfaces of the discrete patches of second acquisition layers with a predetermined pattern of light extending in the cross direction; sensing distortions in patterns of the light reflected from the first surfaces of the discrete patches of second acquisition layers with the sensor to triangulate changes in elevation of the first surfaces of the discrete patches of second acquisition layers; and creating a profile representing a surface topography of discrete patches of second acquisition layers from the triangulated changes in elevation.

In yet another form, a method for assembling disposable absorbent articles, wherein each absorbent article includes a topsheet, a backsheet, and a liquid acquisition layer and an absorbent core disposed between the topsheet and the backsheet, includes the steps of: advancing a topsheet web in machine direction, the topsheet web having a first surface and an opposing second surface, and defining a width in a cross direction; combining a liquid acquisition layer with the topsheet web, wherein the liquid acquisition layer includes a first surface and an opposing second surface, and wherein the first surface of the liquid acquisition layer is positioned in a facing relationship with the second surface of the topsheet web; providing an embossing nip between a rotating patterned embossing roll and a rotating anvil roll; and embossing a pattern in the topsheet web by advancing the combined topsheet web and liquid acquisition layer through the embossing nip; advancing the combined topsheet web and liquid acquisition layer past a sensor; illuminating at least one of the first surface and the second surface of the topsheet web with a predetermined pattern of light extending in the cross direction; sensing distortions in patterns of the light reflected from the topsheet web with the sensor to triangulate changes in elevation of the first surface of the topsheet web; and creating a profile representing a surface topography of first surface of the topsheet web from the triangulated changes in elevation.

BRIEF DESCRIPTION OF THE DRAWINGS

FIG. 14A is a schematic side view another embodiment of an apparatus for assembling components of an absorbent article.

DETAILED DESCRIPTION OF THE INVENTION

Figure 1:
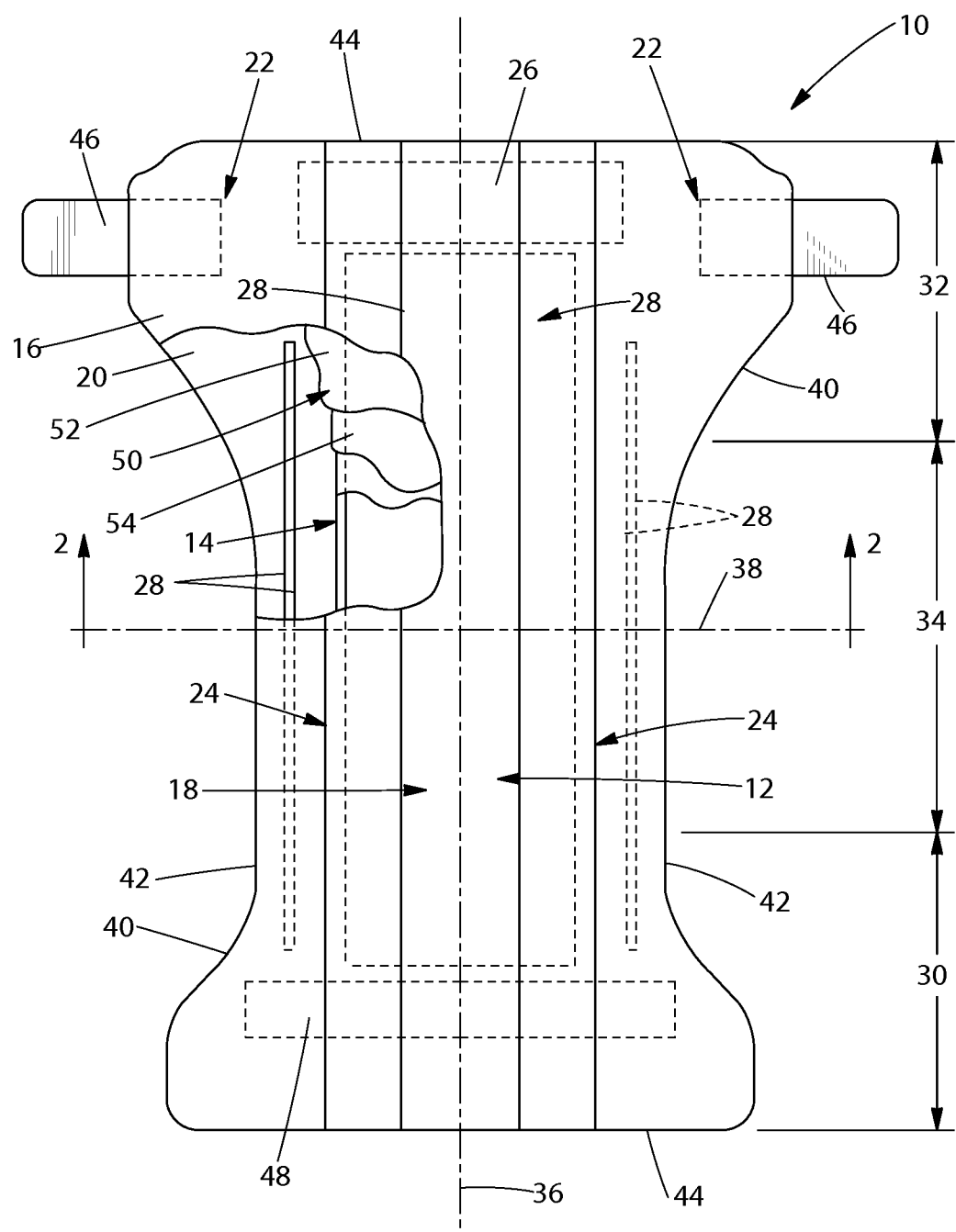
FIG. 1 is a plan view of a diaper.

The following term explanations may be useful in understanding the present disclosure:

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure that may be disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core may be substantially cellulose free. The absorbent core does not include an acquisition system, a topsheet, or a backsheet of the absorbent article. In some embodiments, the absorbent core may consist essentially of the one or more substrates, the absorbent polymer material, the thermoplastic composition, and optionally the cover layer.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

"Absorbent particulate polymer material area" as used herein refers to the area of the core wherein a first substrate and a second substrate are separated by a multiplicity of superabsorbent particles.

"Airfelt" is used herein to refer to comminuted wood pulp, which is a form of cellulosic fiber.

The term "body facing surface" and "body facing side" refer to surfaces of absorbent articles and/or components thereof which face a wearer's body when the absorbent articles are worn, and the term "garment facing surface" and "garment facing side" refer to surfaces of absorbent articles and/or components thereof that face away from a wearer's body when the absorbent articles are worn. Absorbent articles and components thereof, including the topsheet, backsheet, absorbent core, and any individual materials of their components, have a body facing surface and/or side and a garment facing surface and/or side.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes a "pant" which is defined below.

"Fiber" and "filament" are used interchangeably.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "machine direction" (MD) is used herein to refer to the direction of material flow through a process. In addition, relative placement and movement of material can be described as flowing in the machine direction through a process from upstream in the process to downstream in the process. The term "cross direction" (CD) is used herein to refer to a direction that is generally perpendicular to the machine direction.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Example pants are disclosed in U.S. Pat. Nos. 4,940,464; 5,092,861; 5,246, 433; 5,569,234; 5,897,545; 5,957,908; 6,120,487; and 6,120,489 and U.S. Patent Publication No. 2003/0233082 A1.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" as used herein indicates that within the absorbent particulate polymer material area wherein a first substrate and second substrate are separated by a multiplicity of superabsorbent particles. It is recognized that there may be minor incidental contact areas between the first substrate and second substrate within the absorbent particulate polymer material area.

"Thermoplastic adhesive material" as used herein is understood to comprise a polymer composition from which fibers are formed and applied to the superabsorbent material with the intent to immobilize the superabsorbent material in both the dry and wet state. The thermoplastic adhesive material of the present disclosure forms a fibrous network over the superabsorbent material.

"Thickness" and "caliper" are used herein interchangeably.

The present disclosure relates to methods and apparatuses for making absorbent articles with absorbent structures, and in particular, sensing distortions in patterns of reflected light to create profiles representing surface topographies of absorbent structures during the manufacture of absorbent articles. As discussed in more detail below, absorbent articles, such as diapers may have absorbent structures that include a liquid acquisition layer and a substantially cellulose free absorbent core disposed between a topsheet and a backsheet. Aspects of the methods according to the present disclosure relate to the fabrication of absorbent articles wherein an inspection system may be configured to interact with, monitor, and/or control the converting line. The inspection system may include sensors arranged adjacent an advancing absorbent structure on a converting line and may communicate with the controller. Based on such communications, the controller may monitor and affect various operations on the converting line. The inspection systems herein may also include a radiation source that illuminates a surface of an absorbent structure with a predetermined pattern of light extending in the cross direction CD. The sensor may include a lens adapted to receive light reflected from the absorbent structure. In turn, the sensor senses distortions in patterns of light reflected from the illuminated surface of the absorbent structure and triangulates changes in elevation of the illuminated surface of the absorbent structure relative to the sensor. Based on the triangulated changes in elevation, the sensor creates a profile representing a surface topography of the illuminated surface of the absorbent structure.

The following provides a general description of various types of absorbent articles that may be produced with the methods and apparatuses disclosed herein to help provide additional context to the subsequent discussion of the process embodiments.

FIG. 1 is a plan view of a diaper 10 is shown in a flat out, uncontracted state (i.e., without elastic induced contraction) and with portions of the diaper 10 are cut away to more clearly show the underlying structure of the diaper 10. A portion of the diaper 10 that contacts a wearer is facing the viewer in FIG. 1.

As shown in FIG. 1, the diaper 10 may include a chassis 12 having an outer covering 16 including a topsheet 18, which may be liquid pervious, and/or a backsheet 20, which may be liquid impervious. An absorbent core 14 may be encased between the topsheet 18 and the backsheet 20. The chassis 12 may also include side panels 22, elasticized leg cuffs 24, and an elastic waist feature 26. The leg cuffs 24 and the elastic waist feature 26 may each include elastic members 28. One end portion of the diaper 10 may be configured as a first waist region 30 of the diaper 10, and an opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with a longitudinal axis 36 and a lateral axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the lateral axis 38 of the diaper 10. The chassis 12 may also comprise a fastening system, which may include at least one fastening member 46 and at least one stored landing zone 48. The diaper 20 may also include such other features such as front and rear ear panels, waist cap features, elastics and the like to provide better fit, as well as containment and aesthetic characteristics. Such additional features are described, for example, in U.S. Pat. Nos. 3,860,003 and 5,151,092.

A portion of the first waist region 30 may be attached by the fastening member 46 to at least a portion of the second waist region 32 to form leg opening(s) and an article waist opening. In some embodiments, the diaper 10 may be provided with a re-closable fastening system. In some embodiments, the diaper 10 may include a re-closable fastening system joined to the chassis for securing the diaper to a wearer. In some embodiments, the diaper 10 may include at least two side panels joined to the chassis and to each other to form a pant.

It is to be appreciated that the topsheet 18, the backsheet 20, and the absorbent core 14 may be assembled in a variety of configurations, such as for example as described generally in U.S. Pat. Nos. 5,554,145; 5,569,234; and 6,004,306. The topsheet 18 in FIG. 1 may be fully or partially elasticized or may be foreshortened to provide a void space between the topsheet 18 and the absorbent core 14. Exemplary structures including elasticized or foreshortened topsheets are described in more detail in U.S. Pat. Nos. 5,037,416 and 5,269,775. The backsheet 20 may be joined with the topsheet 18. The backsheet 20 may prevent the exudates absorbed by the absorbent core 14 and contained within the diaper 10 from soiling other external articles that may contact the diaper 10, such as bed sheets and undergarments. In certain embodiments, the backsheet 20 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746. Other breathable backsheets including nonwoven webs and apertured formed films are described in U.S. Pat. No. 5,571,096.

Figure 2:
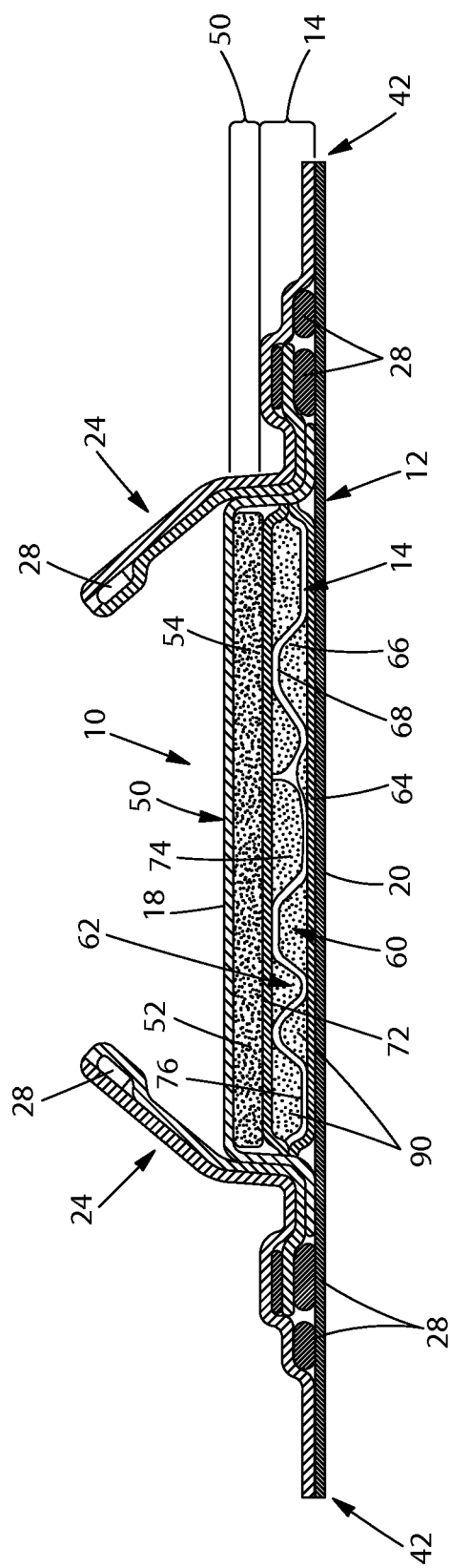
FIG. 2 is a cross sectional view of the diaper shown in FIG. 1 taken along the sectional line 2-2 of FIG. 1.

FIG. 2 is a cross sectional view of the diaper in FIG. 1 taken along the line 2-2. As shown in FIG. 2, the topsheet 18 may define an inner, body facing surface, and the backsheet may define an outer, garment facing surface of the diaper 10. And the absorbent core 14 may be positioned between the topsheet and the backsheet. The diaper 10 may also include an acquisition system 50 disposed between the liquid permeable topsheet 18 and a wearer facing side of the absorbent core 14. The acquisition system 50 may be in direct contact with the absorbent core. The acquisition system 50 (also referred to herein as a liquid acquisition layer 50) may comprise a single layer or multiple layers, such as an upper acquisition layer 52 (also referred to herein as a first acquisition layer 52) facing towards the wearer's skin and a lower acquisition layer 54 (also referred to herein as a second acquisition layer 54) facing the garment of the wearer. In some embodiments, the acquisition system 50 may function to receive a surge of liquid, such as a gush of urine. In other words, the acquisition system 50 may serve as a temporary reservoir for liquid until the absorbent core 14 can absorb the liquid. Exemplary acquisition systems and associated manufacturing processes are described in U.S. Pat. Nos. 8,603,277 and 8,568,566; U.S. Patent Publication No. US2012/0316046 A1; and U.S. patent application Ser. No. 14/100,083, filed on Dec. 9, 2013, all of which are hereby incorporated by reference herein.

In some embodiments, the acquisition system 50 may include chemically cross-linked cellulosic fibers. Such cross-linked cellulosic fibers may have various absorbency properties. Exemplary chemically cross-linked cellulosic fibers are disclosed in U.S. Pat. No. 5,137,537. Citric acid is an exemplary cross-linking agent. In some embodiments, polyacrylic acids may be used. In some embodiments, the cross-linked cellulosic fibers may be crimped, twisted, or curled, or a combination thereof including crimped, twisted, and curled.

In some embodiments, one or both of the upper acquisition layer 52 and lower acquisition layer 54 may include a nonwoven, which may be hydrophilic. Further, according to some embodiments, one or both of the upper acquisition layer 52 and lower acquisition layer 54 may comprise chemically cross-linked cellulosic fibers, which may or may not form part of a nonwoven material. In some embodiments, the upper acquisition layer 52 may comprise a nonwoven, without the cross-linked cellulosic fibers, and the lower acquisition layer 54 may comprise the chemically cross-linked cellulosic fibers. Further, in some embodiments, the lower acquisition layer 54 may comprise the chemically cross-linked cellulosic fibers mixed with other fibers such as natural or synthetic polymeric fibers. According to some embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof.

Suitable nonwoven materials for the upper acquisition layer 52 and lower acquisition layer 54 include, but are not limited to SMS material, comprising a spunbonded, a meltblown and a further spunbonded layer. In certain embodiments, permanently hydrophilic nonwovens, and in particular, nonwovens with durably hydrophilic coatings are desirable. Another suitable embodiment comprises a SMMS-structure. In certain embodiments, the nonwovens are porous.

In certain embodiments, suitable nonwoven materials may include, but are not limited to synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in U.S. Patent Publication No. 2005/0159720. Another way to produce nonwovens with durably hydrophilic coatings is to coat the nonwoven with hydrophilic nanoparticles as described in U.S. Pat. No. 7,112,621; U.S. Patent Publication No. US2004/0158212A1; and PCT Publication No. WO 02/064877. Other nonwovens are described in U.S. Pat. Nos. 6,645,569; 6,863,933; and 7,112,621 as well as U.S. Patent Publication Nos. US2003/0148684A1 and US2005/0008839A1.

In some embodiments, the upper acquisition layer 52 may include a material that provides recovery when external pressure is applied and removed. Further, according to some embodiments, the upper acquisition layer 52 may comprise a blend of different fibers selected, for example from the types of polymeric fibers described above. In some embodiments, at least a portion of the fibers may exhibit a spiral-crimp which has a helical shape. In some embodiments, the upper acquisition layer 52 may comprise fibers having different degrees or types of crimping, or both. Different types of crimps include, but are not limited to a 2D crimp or "flat crimp" and a 3D or spiral-crimp. According to some embodiments, the fibers may include bi-component fibers, which are individual fibers each comprising different materials, such as a first and a second polymeric material.

The upper acquisition layer 52 may be stabilized by a latex binder, for example a styrene-butadiene latex binder (SB latex), in a certain embodiment. Processes for obtaining such lattices are described, for example, in EP Patent Publication No. EP0149880A2 and U.S. Patent Publication No. US2003/0105190. In some embodiments, SB latex is available under the trade name GENFLO™ 3160 (OMNOVA Solutions Inc.; Akron, Ohio).

Figure 3:
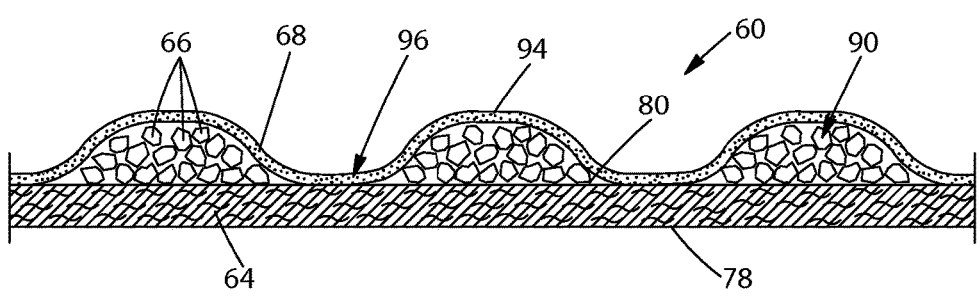
FIG. 3 is a partial cross sectional view of an absorbent core layer.
Figure 4:
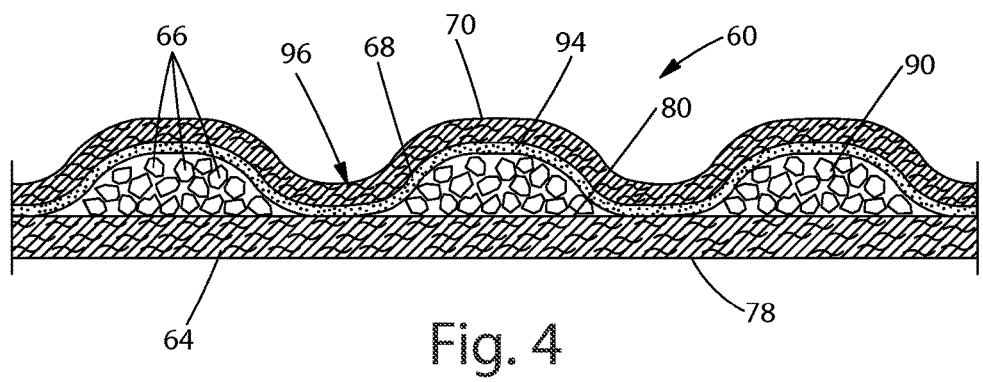
FIG. 4 is a partial cross sectional view of an absorbent core layer.
Figure 5:
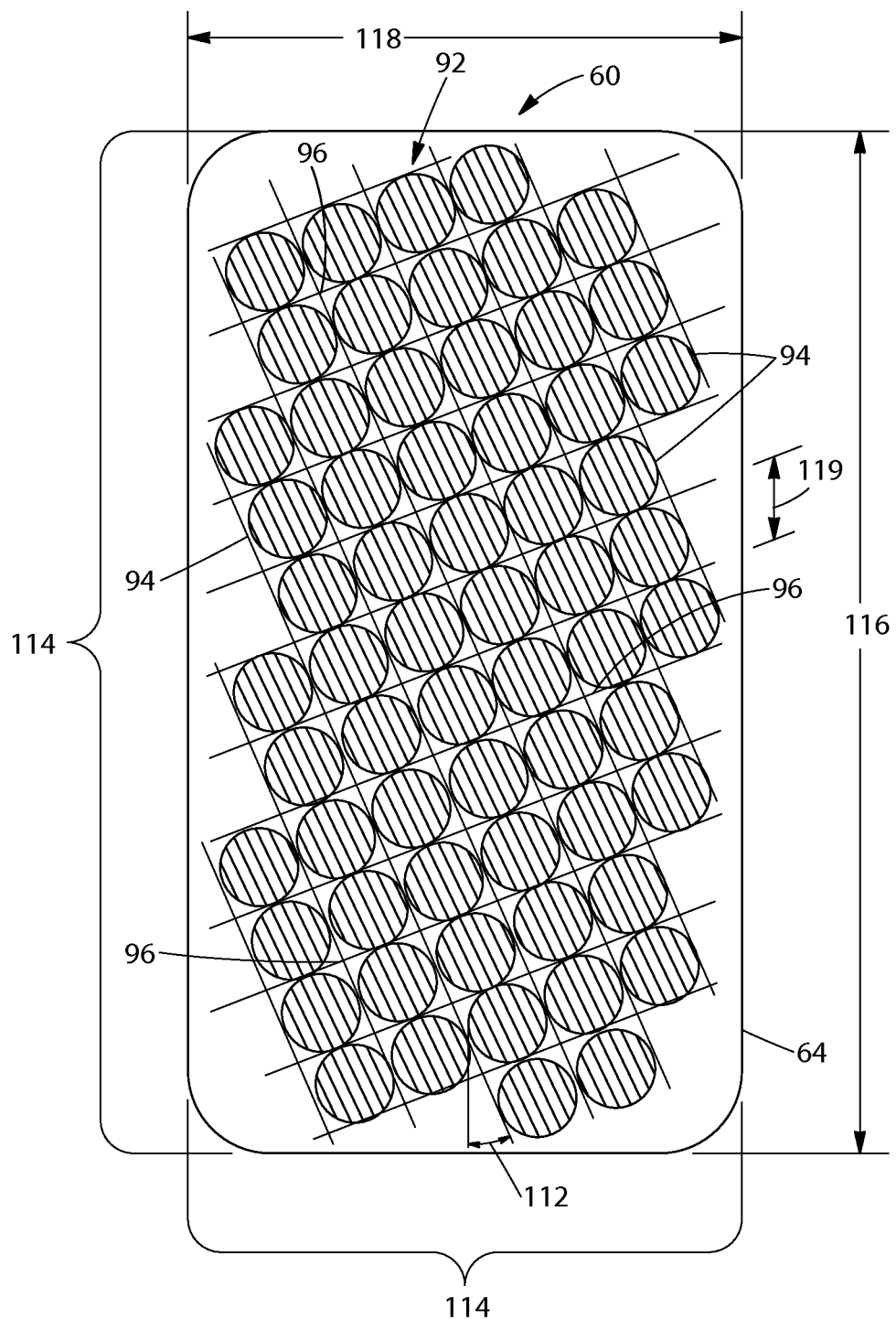
FIG. 5 is a plan view of the absorbent core layer illustrated in FIG. 3.
Figure 6:
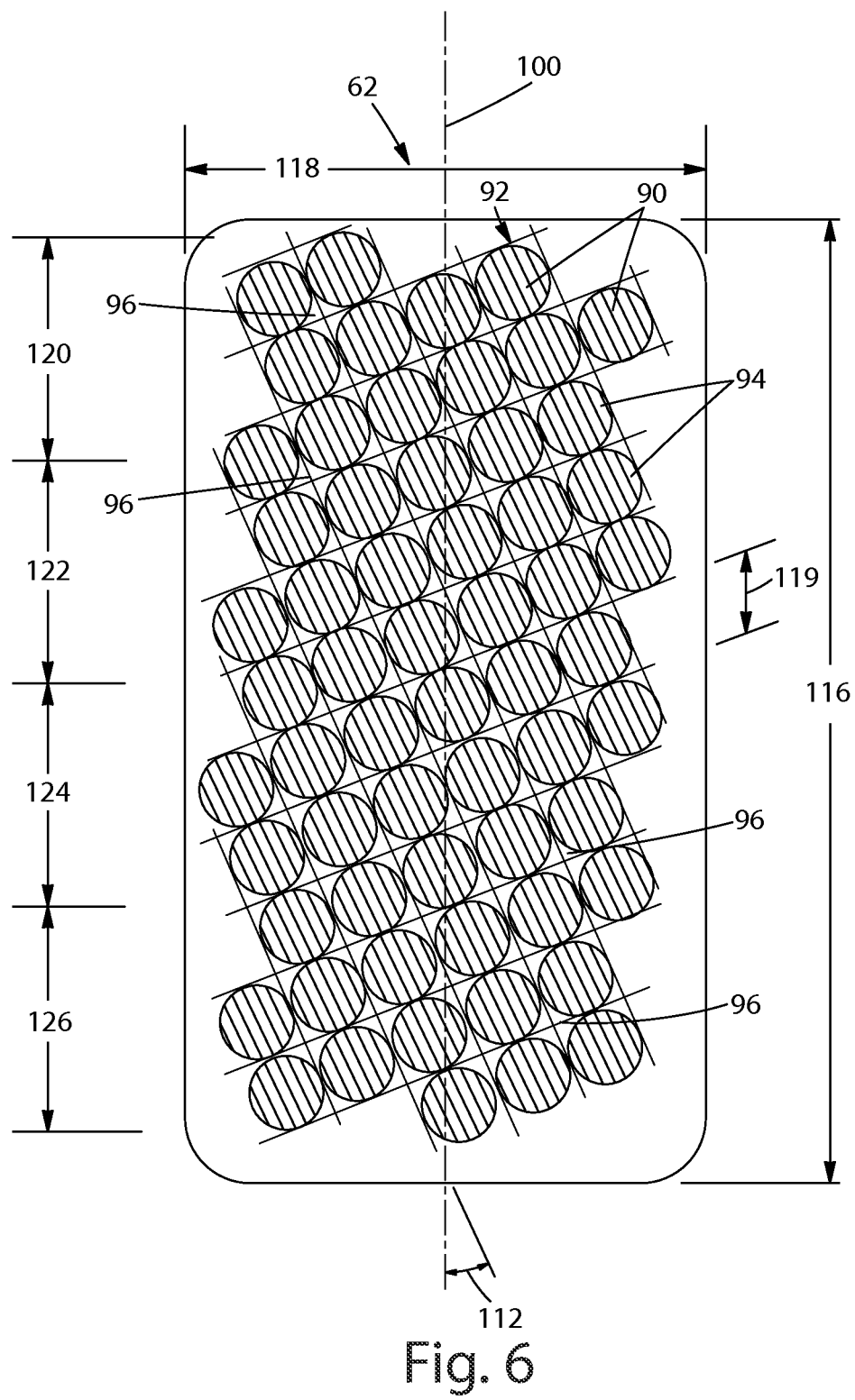
FIG. 6 is a plan view of a second absorbent core layer.

The absorbent core 14, such as shown in FIGS. 1-8 may be disposed between the topsheet 18 and the backsheet 20 and may include two layers, a first absorbent layer 60 and a second absorbent layer 62. As shown in FIG. 3, the first absorbent layer 60 of the absorbent core 14 may include a substrate 64, an absorbent particular polymer material 66 on the substrate 64, and a thermoplastic composition 68 on the absorbent particular polymer material 66 and at least portions of the first substrate 64 as an adhesive for covering and immobilizing the absorbent particular polymer material 66 on the first substrate 64. In some embodiments, such as illustrated in FIG. 4, the first absorbent layer 60 of the absorbent core 14 may also include a cover layer 70 on the thermoplastic composition 68. The cover layer 70 shown in FIG. 4 may include the same material as the substrates 64 and 72, or may include a different material. In certain embodiments, the materials of the cover layer 70 are the nonwoven materials, such as the materials described above as useful for the substrates 64 and 72. Exemplary absorbent cores and associated manufacturing processes are described in U.S. Pat. Nos. 8,603,277 and 8,568,566; U.S. Patent Publication No. US2012/0316046 A1; and U.S. patent application Ser. No. 14/100,083, filed on Dec. 9, 2013, all of which are hereby incorporated by reference herein.

As shown in FIG. 2, the second absorbent layer 62 of the absorbent core 14 may also include a substrate 72, an absorbent particulate polymer material 74 on the second substrate 72, and a thermoplastic composition 76 on the absorbent particulate polymer material 74 and at least a portion of the second substrate 72 for immobilizing the absorbent particulate polymer material 74 on the second substrate 72. Although not illustrated, the second absorbent layer 62 may also include a cover layer such as the cover layer 70 illustrated in FIG. 4.

The substrate 64 of the first absorbent layer 60 may be referred to as a dusting layer and has a first surface 78 which faces the backsheet 20 of the diaper 10 and a second surface 80 which faces the absorbent particulate polymer material 66. The substrate 72 of the second absorbent layer 62 may be referred to as a core cover and has a first surface 82 facing the topsheet 18 of the diaper 10 and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14. In some embodiments, the substrates 64 and 72 of the first and second absorbent layers 60 and 62 may be a nonwoven material, such as those nonwoven materials described above.

As shown in FIGS. 1-8, the absorbent particulate polymer material 66 and 74 may be deposited on the respective substrates 64 and 72 of the first and second absorbent layers 60 and 62 in clusters 90 of particles to form a grid pattern 92 comprising land areas 94 and junction areas 96 between the land areas 94. As defined herein, land areas 94 are areas where the thermoplastic adhesive material does not contact the nonwoven substrate or the auxiliary adhesive directly; junction areas 96 are areas where the thermoplastic adhesive material does contact the nonwoven substrate or the auxiliary adhesive directly. The junction areas 96 in the grid pattern 92 contain little or no absorbent particulate polymer material 66 and 74. The land areas 94 and junction areas 96 can have a variety of shapes including, but not limited to, circular, oval, square, rectangular, triangular, and the like.

Figure 8:
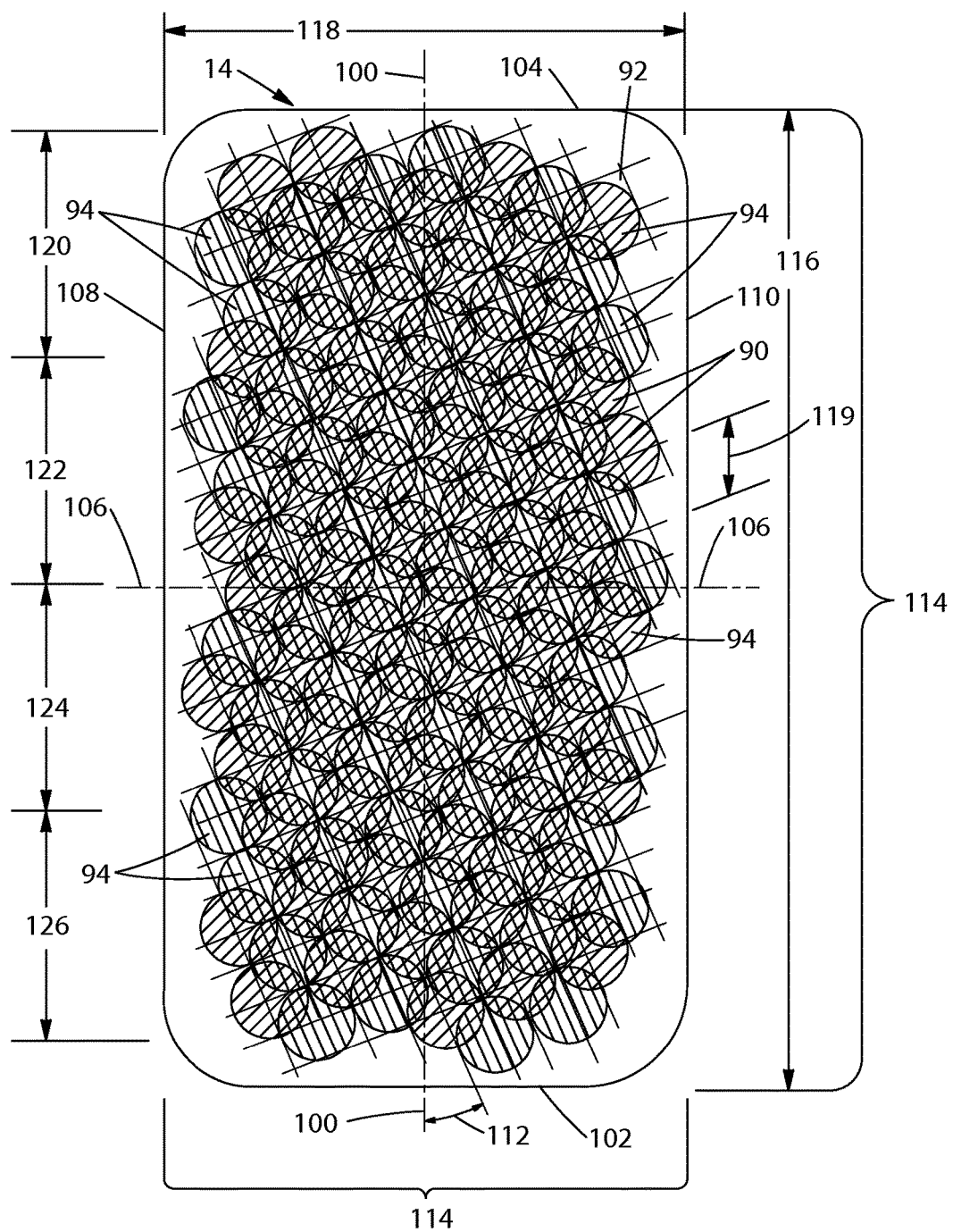
FIG. 8 is a plan view of the absorbent core illustrated in FIGS. 7a and 7b.

The grid pattern shown in FIG. 8 is a square grid with regular spacing and size of the land areas. Other grid patterns including hexagonal, rhombic, orthorhombic, parallelogram, triangular, rectangular, and combinations thereof may also be used. The spacing between the grid lines may be regular or irregular.

As shown in FIG. 8, the absorbent core 14 has a longitudinal axis 100 extending from a rear end 102 to a front end 104 and a lateral axis 106 perpendicular to the longitudinal axis 100 extending from a first edge 108 to a second edge 110. The grid pattern 92 of absorbent particulate polymer material clusters 90 is arranged on the substrates 64 and 72 of the respective absorbent layers 60 and 62 such that the grid pattern 92 formed by the arrangement of land areas 94 and junction areas 96 forms a pattern angle 112. The pattern angle 112 may be 0, greater than 0, or 15 to 30 degrees, or from about 5 to about 85 degrees, or from about 10 to about 60 degrees, or from about 15 to about 30 degrees.

Figure 7A:
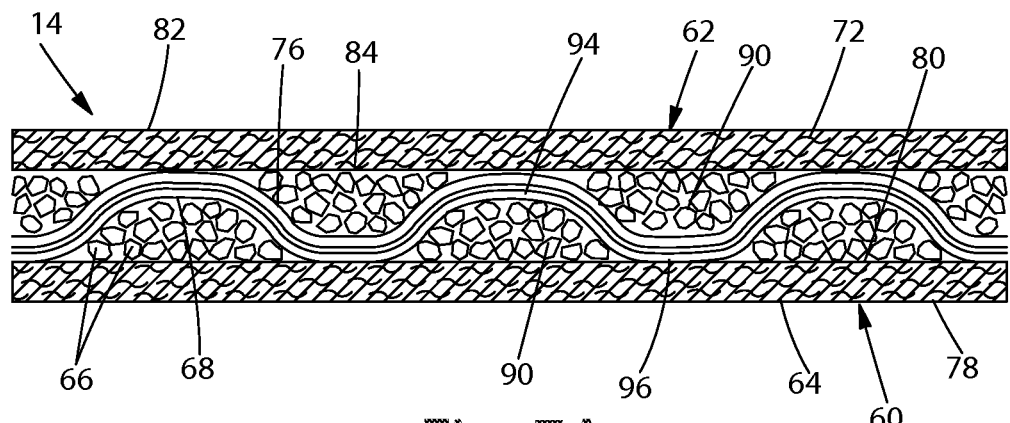
FIG. 7A is a partial sectional view of an absorbent core comprising a combination of the first and second absorbent core layers illustrated in FIGS. 5 and 6.
Figure 7B:
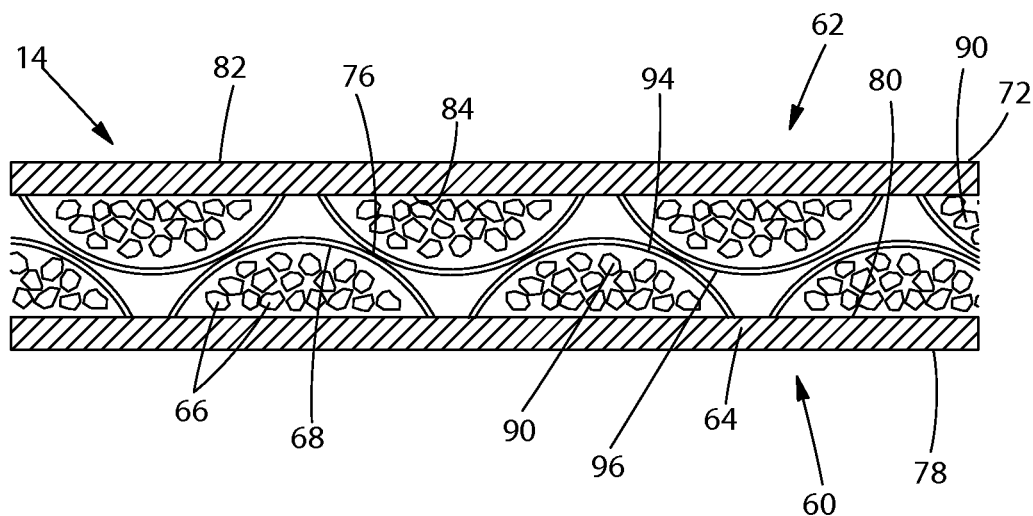
FIG. 7B is a partial sectional view of an absorbent core comprising a combination of the first and second absorbent core layers illustrated in FIGS. 5 and 6.

As shown in FIGS. 7a, 7b, and 8, the first and second layers 60 and 62 may be combined to form the absorbent core 14. The absorbent core 14 has an absorbent particulate polymer material area 114 bounded by a pattern length 116 and a pattern width 118. The extent and shape of the absorbent particulate polymer material area 114 may vary depending on the desired application of the absorbent core 14 and the particular absorbent article in which it may be incorporated. In some embodiments, the absorbent particulate polymer material area 114 extends substantially entirely across the absorbent core 14, such as is illustrated in FIG. 8.

The first and second absorbent layers 60 and 62 may be combined together to form the absorbent core 14 such that the grid patterns 92 of the respective first and second absorbent layers 62 and 64 are offset from one another along the length and/or width of the absorbent core 14. The respective grid patterns 92 may be offset such that the absorbent particulate polymer material 66 and 74 is substantially continuously distributed across the absorbent particulate polymer area 114. In some embodiments, absorbent particulate polymer material 66 and 74 may be substantially continuously distributed across the absorbent particulate polymer material area 114 despite the individual grid patterns 92 comprising absorbent particulate polymer material 66 and 74 discontinuously distributed across the first and second substrates 64 and 72 in clusters 90. In some embodiments, the grid patterns may be offset such that the land areas 94 of the first absorbent layer 60 face the junction areas 96 of the second absorbent layer 62 and the land areas of the second absorbent layer 62 face the junction areas 96 of the first absorbent layer 60. When the land areas 94 and junction areas 96 are appropriately sized and arranged, the resulting combination of absorbent particulate polymer material 66 and 74 is a substantially continuous layer of absorbent particular polymer material across the absorbent particulate polymer material area 114 of the absorbent core 14. In some embodiments, respective grid patterns 92 of the first and second absorbent layer 60 and 62 may be substantially the same.

In some embodiments, such as shown in FIG. 8, the amount of absorbent particulate polymer material 66 and 74 may vary along the length 116 of the grid pattern 92. The grid pattern may be divided into absorbent zones 120, 122, 124, and 126, in which the amount of absorbent particulate polymer material 66 and 74 varies from zone to zone. As used herein, "absorbent zone" refers to a region of the absorbent particulate polymer material area having boundaries that are perpendicular to the longitudinal axis shown in FIG. 8. The amount of absorbent particulate polymer material 66 and 74 may, in a certain embodiment, gradually transition from one of the plurality of absorbent zones 120, 122, 124, and 126 to another.

The amount of absorbent particulate polymer material 66 and 74 present in the absorbent core 14 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core 14 consists essentially of the first and second substrates 64 and 72, the absorbent particulate polymer material 66 and 74, and the thermoplastic adhesive composition 68 and 76. In some embodiments, the absorbent core 14 may be substantially cellulose free.

The absorbent particulate polymer material area may have a relatively narrow width in the crotch area of the absorbent article for increased wearing comfort.

It some absorbent articles, such as diapers, liquid discharge from the wearer may occur predominately in the front half of the diaper. The front half of the absorbent core 14 may therefore comprise most of the absorbent capacity of the core. Thus, according to certain embodiments, the front half of said absorbent core 14 may comprise more than about 60% of the superabsorbent material, or more than about 65%, 70%, 75%, 80%, 85%, or 90% of the superabsorbent material.

In certain embodiments, the absorbent core 14 may further comprise any absorbent material that is generally compressible, conformable, non-irritating to the wearer's skin, and capable of absorbing and retaining liquids such as urine and other certain body exudates. In such embodiments, the absorbent core 14 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 14 may further comprise minor amounts (typically less than about 10%) of materials, such as adhesives, waxes, oils and the like. Exemplary absorbent structures for use as the absorbent assemblies are described in U.S. Pat. Nos. 4,610,678; 4,834,735; 4,888,231; 5,260,345; 5,387,207; and 5,397,316.

The thermoplastic adhesive material 68 and 76 may cover and at least partially immobilize the absorbent particulate polymer material 66 and 74. In some embodiments, the thermoplastic adhesive material 68 and 76 can be disposed essentially uniformly within the absorbent particulate polymer material 66 and 74, between the polymers. In some embodiments, the thermoplastic adhesive material 68 and 76 may be provided as a fibrous layer which is at least partially in contact with the absorbent particulate polymer material 66 and 74 and partially in contact with the substrate layers 64 and 72 of the first and second absorbent layers 60 and 62. FIGS. 3, 4, and 7 show such a structure wherein the absorbent particulate polymer material 66 and 74 is provided as a discontinuous layer, and a layer of fibrous thermoplastic adhesive material 68 and 76 is laid down onto the layer of absorbent particulate polymer material 66 and 74, such that the thermoplastic adhesive material 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. This imparts an essentially three-dimensional structure to the fibrous layer of thermoplastic adhesive material 68 and 76, which in itself is essentially a two-dimensional structure of relatively small thickness, as compared to the dimension in length and width directions. In other words, the thermoplastic adhesive material 68 and 76 undulates between the absorbent particulate polymer material 68 and 76 and the second surfaces of the substrates 64 and 72.

Thereby, the thermoplastic adhesive material 68 and 76 may provide cavities to cover the absorbent particulate polymer material 66 and 74, and thereby immobilizes this material. In a further aspect, the thermoplastic adhesive material 68 and 76 bonds to the substrates 64 and 72 and thus affixes the absorbent particulate polymer material 66 and 74 to the substrates 64 and 72. Thus, in accordance with certain embodiments, the thermoplastic adhesive material 68 and 76 immobilizes the absorbent particulate polymer material 66 and 74 when wet. Some thermoplastic adhesive materials will also penetrate into both the absorbent particulate polymer material 66 and 74 and the substrates 64 and 72, thus providing for further immobilization and affixation. Of course, while the thermoplastic adhesive materials disclosed herein provide a much improved wet immobilization (i.e., immobilization of absorbent material when the article is wet or at least partially loaded), these thermoplastic adhesive materials may also provide a very good immobilization of absorbent material when the absorbent core 14 is dry. The thermoplastic adhesive material 68 and 76 may also be referred to as a hot melt adhesive.

The absorbent core 14 may also include an auxiliary adhesive 137 which is discussed in more detail below with reference to FIG. 11. The auxiliary adhesive 137 may be deposited on the first substrate 64 and/or second substrate 72 of the respective first and second absorbent layers 60 and 62 before application of the absorbent particulate polymer material 66 and 74 for enhancing adhesion of the absorbent particulate polymer materials 66 and 74 and the thermoplastic adhesive material 68 and 76 to the respective substrates 64 and 72. The auxiliary adhesive 137 may also aid in immobilizing the absorbent particulate polymer material 66 and 74 and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B.

Figure 9:
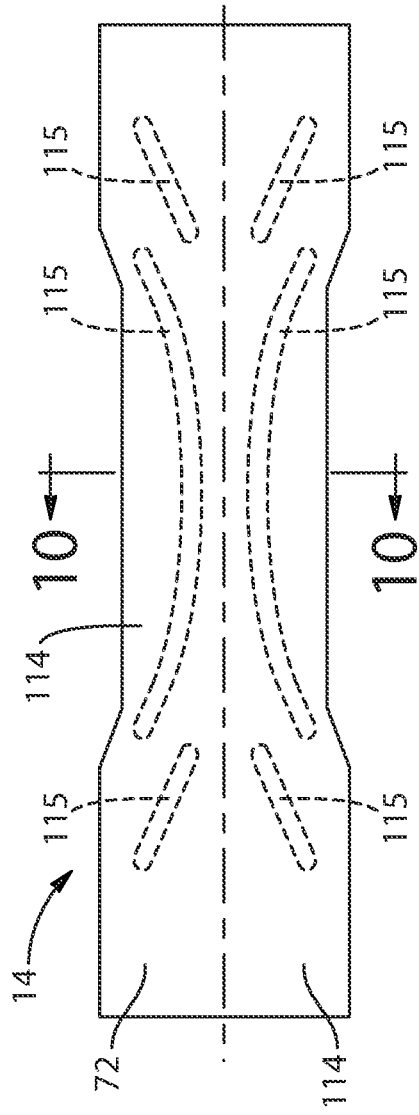
FIG. 9 is a plan view of an absorbent core with channels.
Figure 10:
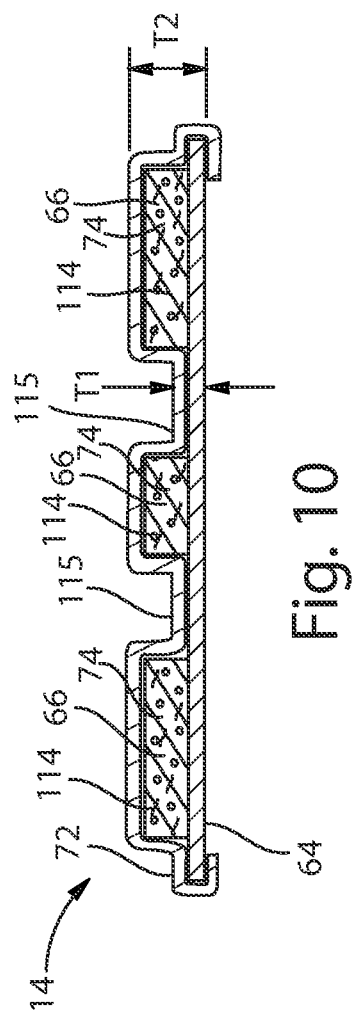
FIG. 10 is a cross sectional view of the absorbent core shown in FIG. 9 taken along the sectional line 10-10 of FIG. 9.

As shown in FIGS. 9 and 10, the absorbent core 14 may also be configured with one or more channel regions 115. In some embodiments, the channel regions 115 may be regions of the absorbent core 14 that are substantially free of absorbent particulate polymer material 66, 74 surround by absorbent particulate polymer material areas 114. In some embodiments, the substrates 64, 72 may be bonded with directly each other in the channel regions 115. In some embodiments, the channel regions 115 may have a first thickness T1 surrounded by absorbent particulate polymer material areas 114 having a second thickness T2, wherein first thickness T1 is less than the second thickness T2. It is to be appreciated that the absorbent core 14 may include various quantities of channel regions 115 having various shapes, widths, and/or lengths. It is to be appreciated that the acquisition system 50 may also include channels that may or not correspond with the channels 115 in the absorbent core 14. For example, the first acquisition layer 52 and/or the second acquisition layer 54 may include channels that may or not correspond with each other and/or with the channels 115 in the absorbent core 14.

It is to be appreciated that the absorbent core may be constructed in various ways. For example, a converting apparatus 300 may include a printing system 130 for making an absorbent core 14 is shown in FIG. 11 and may include a first printing unit 132 for forming the first absorbent layer 60 of the absorbent core 14 and a second printing unit 134 for forming the second absorbent layer 62 of the absorbent core 14. The first printing unit 132 may include a first auxiliary adhesive applicator 136 for applying an auxiliary adhesive 137 to the first substrate 64; a first rotatable support roll 140 for receiving the substrate 64; a hopper 142 for holding absorbent particulate polymer material 66; a printing roll 144 for transferring the absorbent particulate polymer material 66 to the substrate 64; and a thermoplastic adhesive material applicator 146 for applying the thermoplastic adhesive material 68 to the substrate 64 and the absorbent particulate polymer 66 material thereon. The second printing unit 134 may include a second auxiliary adhesive applicator 148 for applying an auxiliary adhesive to the second substrate 72, a second rotatable support roll 152 for receiving the second substrate 72, a second hopper 154 for holding the absorbent particulate polymer material 74, a second printing roll 156 for transferring the absorbent particulate polymer material 74 from the hopper 154 to the second substrate 72, and a second thermoplastic adhesive material applicator 158 for applying the thermoplastic adhesive material 76 to the second substrate 72 and the absorbent particulate polymer material 74 thereon.

The first and second auxiliary applicators 136 and 148 and/or the first and second thermoplastic adhesive material applicators 146 and 158 may apply adhesive in various ways. For example, the first and second auxiliary applicators 136 and 148 and/or the first and second thermoplastic adhesive material applicators 146 and 158 may include nozzle systems that can provide a relatively thin but wide curtain of thermoplastic adhesive material. In some embodiments, the first and second auxiliary applicators 136 and 148 may be slot coat applicators that apply the auxiliary glue 137 to the first and/or second substrates 64, 72 in strips extending along the machine direction MD. In some embodiments, the auxiliary glue strips may be about 0.5 to about 1 mm wide that are spaced about 0.5 to about 2 mm apart from each other along the cross direction CD. The printing system 130 may also include a guide roller 160 for guiding the formed absorbent core from a nip 162 between the first and second rotatable support rolls 140 and 152.

Figure 12:
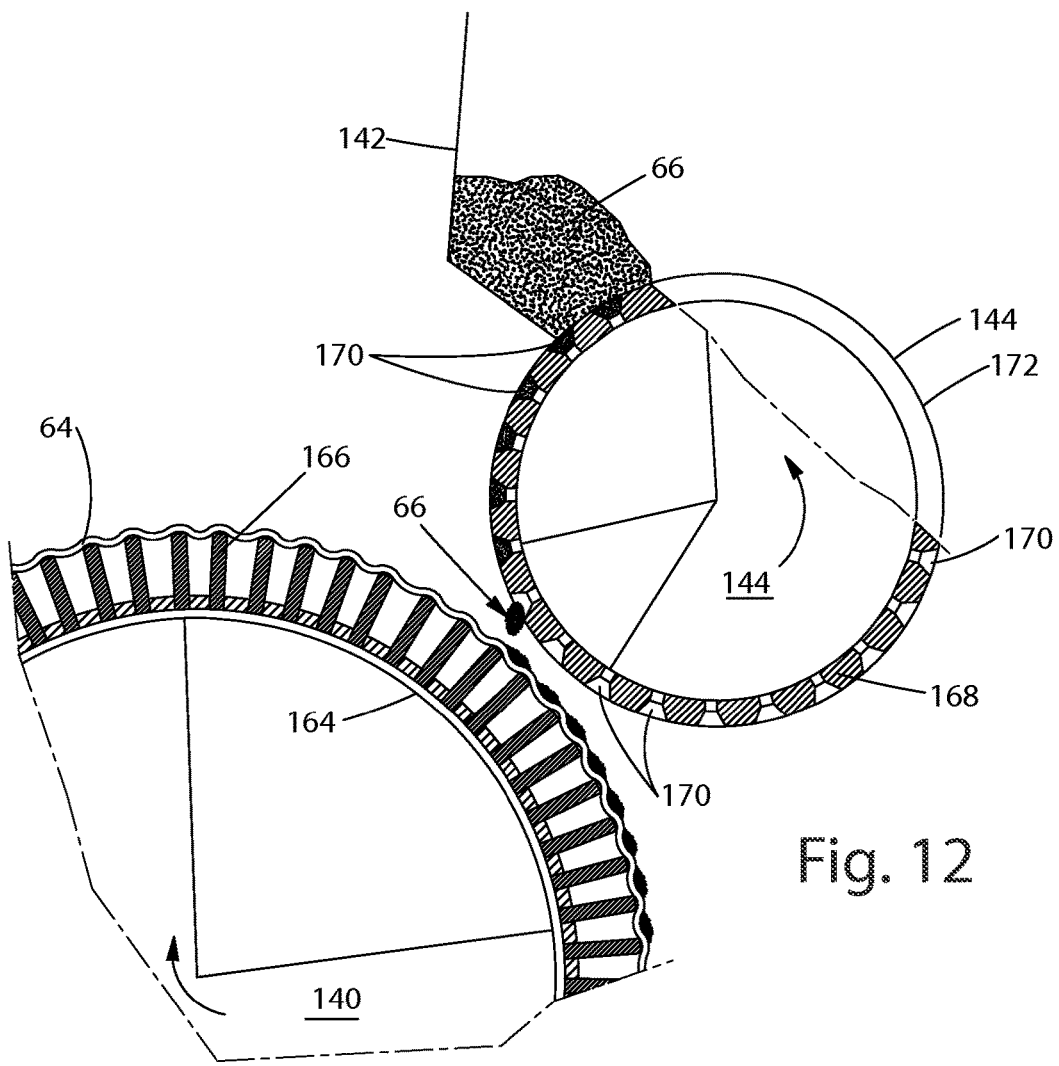
FIG. 12 is a partial sectional view of an apparatus for making an absorbent core.
Figure 13:
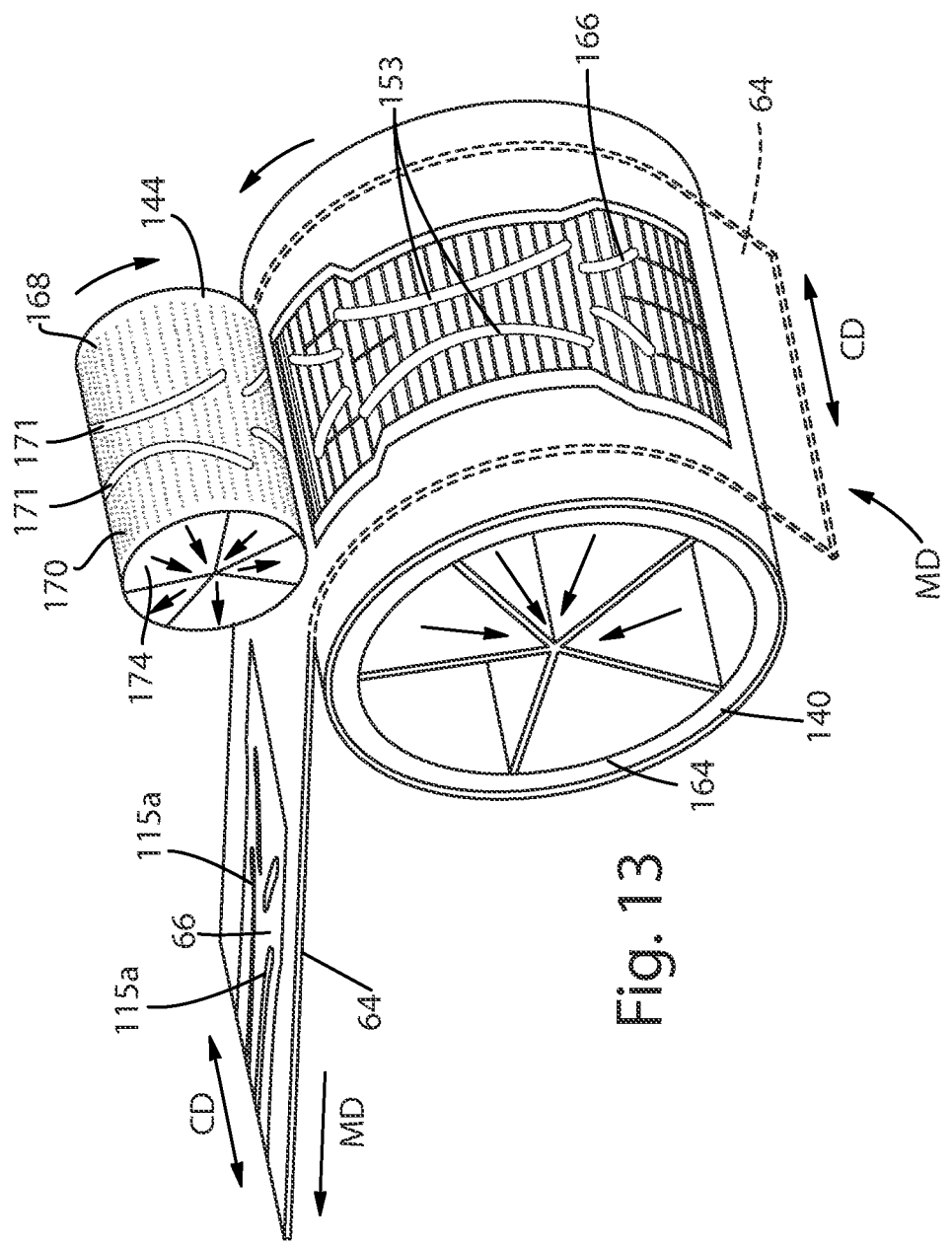
FIG. 13 is a perspective view of a printing roll and supporting roll.

FIGS. 12 and 13 show portions of the first hopper 142, first support roll 140, and first printing roll 144. The first rotatable support roll 140, which may have the same structure as the second rotatable support roll 152, includes a rotatable drum 164 and a peripheral vented support grid 166 for receiving the first substrate 64. As also shown in FIGS. 12 and 13, the first printing roll 144, which may have the same structure as the second printing roll 156, comprises a rotatable drum 168 and a plurality of absorbent particulate polymer material reservoirs 170 in a peripheral surface 172 of the drum 168. The reservoirs 170, such as shown in FIGS. 12 and 13, may have a variety of shapes, including cylindrical, conical, or any other shape. The reservoirs 170 may lead to an air passage 174 in the drum 168 and include a vented cover for holding absorbent particulate polymer material 66 in the reservoir and preventing the absorbent particulate polymer material 66 from falling or being pulled into the air passage 174.

As shown in FIG. 13 the first printing roll 144, which may have the same structure as the second printing roll 156, may include one or more strips 171 that have no void volume, and as such, do not pick up and/or hold absorbent particulate polymer material 66. In addition, the first rotatable support roll 140, which may have the same structure as the second rotatable support roll 152, may include one or more mating strips 153. The strips 171 may be configured to substantially coincide with the mating strips 153. As such, the absorbent particulate polymer material 66, 74 may be deposited selectively on the substrates 64, 72 except for areas that coincide with the mating strips 153 to form absorbent layers on the substrates 64, 72 having regions 115*a* that are substantially free of absorbent material.

Figure 11:
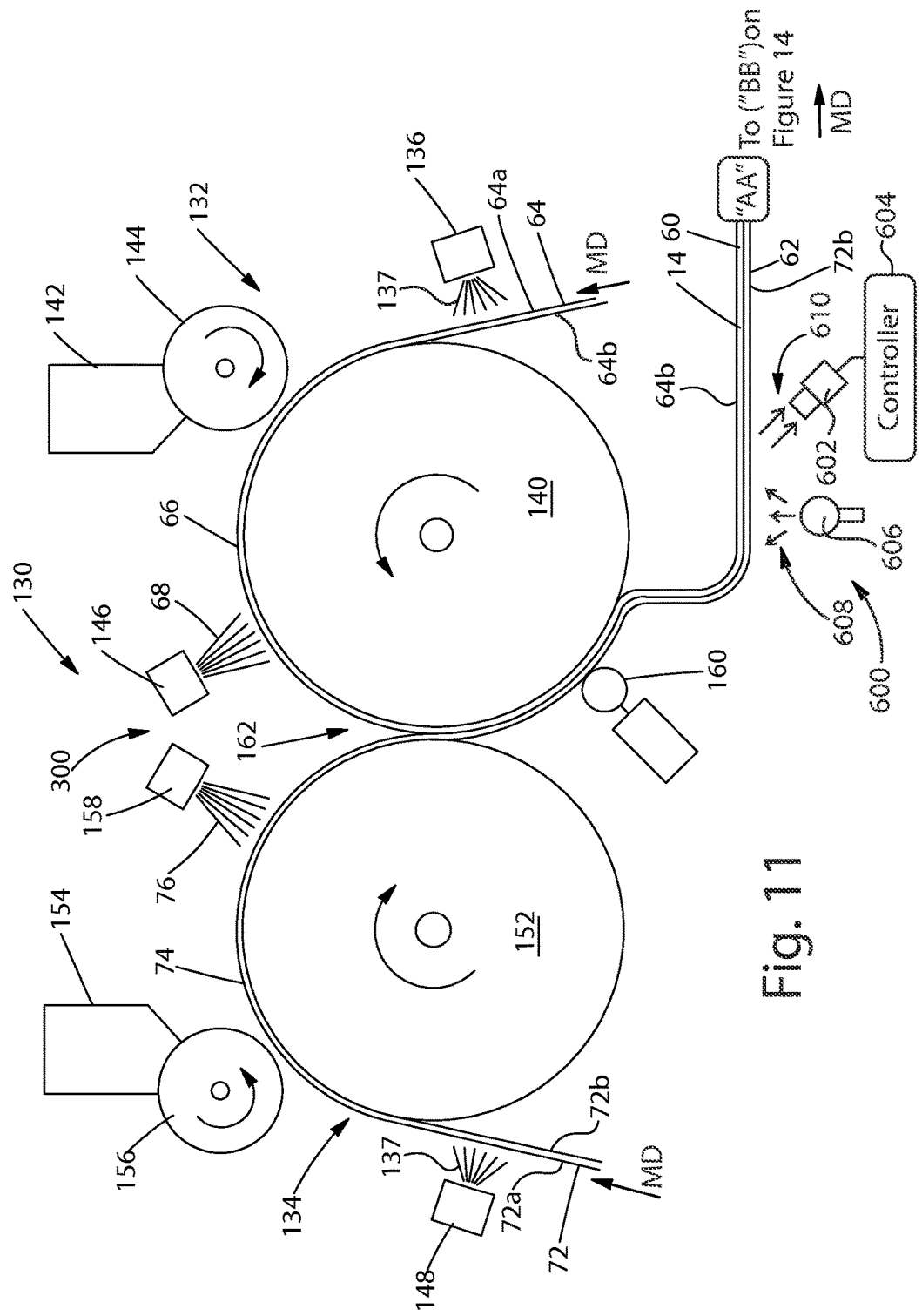
FIG. 11 is a schematic illustration of a process for making an absorbent core.

Referring to FIGS. 11-13, in operation, a first continuous substrate 64 advances in a machine direction MD, and a second continuous substrate 72 advances in a machine direction MD. The first continuous substrate 64 includes a first surface 64*a* and an opposing second surface 64*b*, and defines a width in a cross direction CD. And the second continuous substrate 72 includes a first surface 72*a* and an opposing second surface 72*b*, and defines a width in a cross direction CD. The printing system 130 receives the first and second substrates 64 and 72 into the first and second printing units 132 and 134, respectively. The first substrate 64 advances on the rotating first support roll 140 past the first auxiliary adhesive applicator 136 that applies auxiliary adhesive 137 to the first surface 64*a* of the first substrate 64 in a pattern such as described hereinabove. A vacuum within the first support roll 140 may draw the first substrate 64 against the vertical support grid 166 and hold the first substrate 64 against the first support roll 140. The first support roll 140 then advances the first substrate 64 past the rotating first printing roll 144 that transfers the absorbent particulate polymer material 66 from the first hopper 142 to the first surface 64*a* of the first substrate 64. The first printing roll 144 may hold the absorbent particulate polymer material 66 in the reservoirs 170 and then deliver the absorbent particulate polymer material 66 to the first substrate 64. The support roll 140 then advances the printed first substrate 64 past the thermoplastic adhesive material applicator 146 which applies the thermoplastic adhesive material 68 to cover the absorbent particulate polymer material 66 on the first surface 64*a* of the first substrate 64. With continued reference to FIGS. 11-13, the second rotatable support roll 152 advances the second substrate 72 past the second auxiliary adhesive applicator 148 that applies auxiliary adhesive 137 to the first surface 72*a* of the second substrate 72 in a pattern such as is described hereinabove. The second rotatable support roll 152 then advances the second substrate 72 past the second printing roll 156 which transfers the absorbent particulate polymer material 74 from the second hopper 154 to the first surface 72*a* of the second substrate 72. The second thermoplastic adhesive material applicator 158 then applies the thermoplastic adhesive material 76 to cover the absorbent particulate polymer material 74 on the second substrate 72. The printed first and second substrates 64 and 72 then pass through the nip 162 between the first and second support rolls 140 and 152 for compressing the first absorbent layer 60 and second absorbent layer 62 together to form a continuous length of absorbent cores 14.

It is to be appreciated that various embodiments of diapers can be manufactured according various methods disclosed herein, such as for example disclosed in U.S. Pat. Nos. 8,603,277 and 8,568,566; U.S. Patent Publication Nos. US2008/031621A1 and US2012/0316046 A1; and U.S. patent application Ser. No. 14/100,083, filed on Dec. 9, 2013, all of which are hereby incorporated by reference herein. In some configurations, a cover layer 70 may be placed upon the substrates 64 and 72, the absorbent particulate polymer material 66 and 74, and the thermoplastic adhesive material 68 and 76. In another embodiment, the cover layer 70 and the respective substrate 64 and 72 may be provided from a unitary sheet of material. The placing of the cover layer 70 onto the respective substrate 64 and 72 may then involve the folding of the unitary piece of material.

Figure 14:
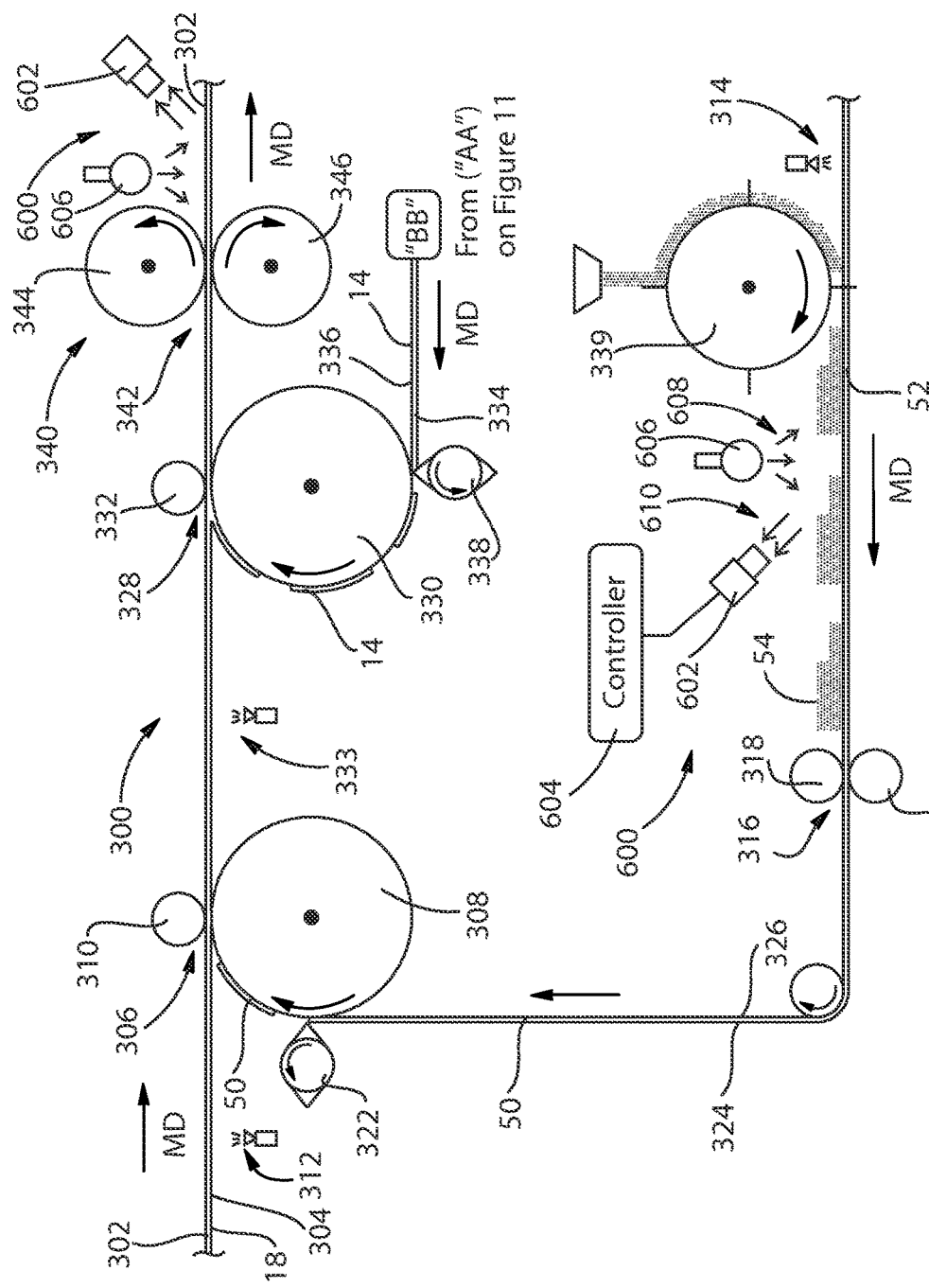
FIG. 14 is a schematic side view an apparatus for assembling components of an absorbent article.

As previously mentioned, the apparatuses and methods according to the present disclosure may be utilized to assemble various components of absorbent articles. For example, FIG. 14 shows a schematic view of a converting apparatus 300 adapted to manufacture diapers 10 having absorbent cores 14 and acquisition layers 50 as discussed above. As such, the method of operation of the converting apparatus 300 may described with reference to the various components of diapers 10 described above and shown in FIGS. 1-10. As described in more detail below, the converting apparatus 300 shown in FIG. 14 operates to advance a continuous topsheet web 18 in a machine direction. A liquid acquisition layer 50 and an absorbent core 14 are combined with the advancing topsheet web 18. The combined continuous topsheet web 18, liquid acquisition layer 50, and absorbent core 14 are then advanced to subsequent converting operations to complete assembly of absorbent articles 10. As shown in FIG. 14, a continuous topsheet web 18 having a first surface 302 and an opposing second surface 304 is combined with a liquid acquisition system or layer 50. More particularly, the topsheet web 18 is advanced in a machine direction MD to a nip 306 defined between a carrier apparatus 308 and roll 310, where the topsheet web 18 and liquid acquisition layer 50 are combined. Before entering the nip 306, adhesive 312 may be applied to the second surface 304 of the topsheet web 18.

Figure 15:
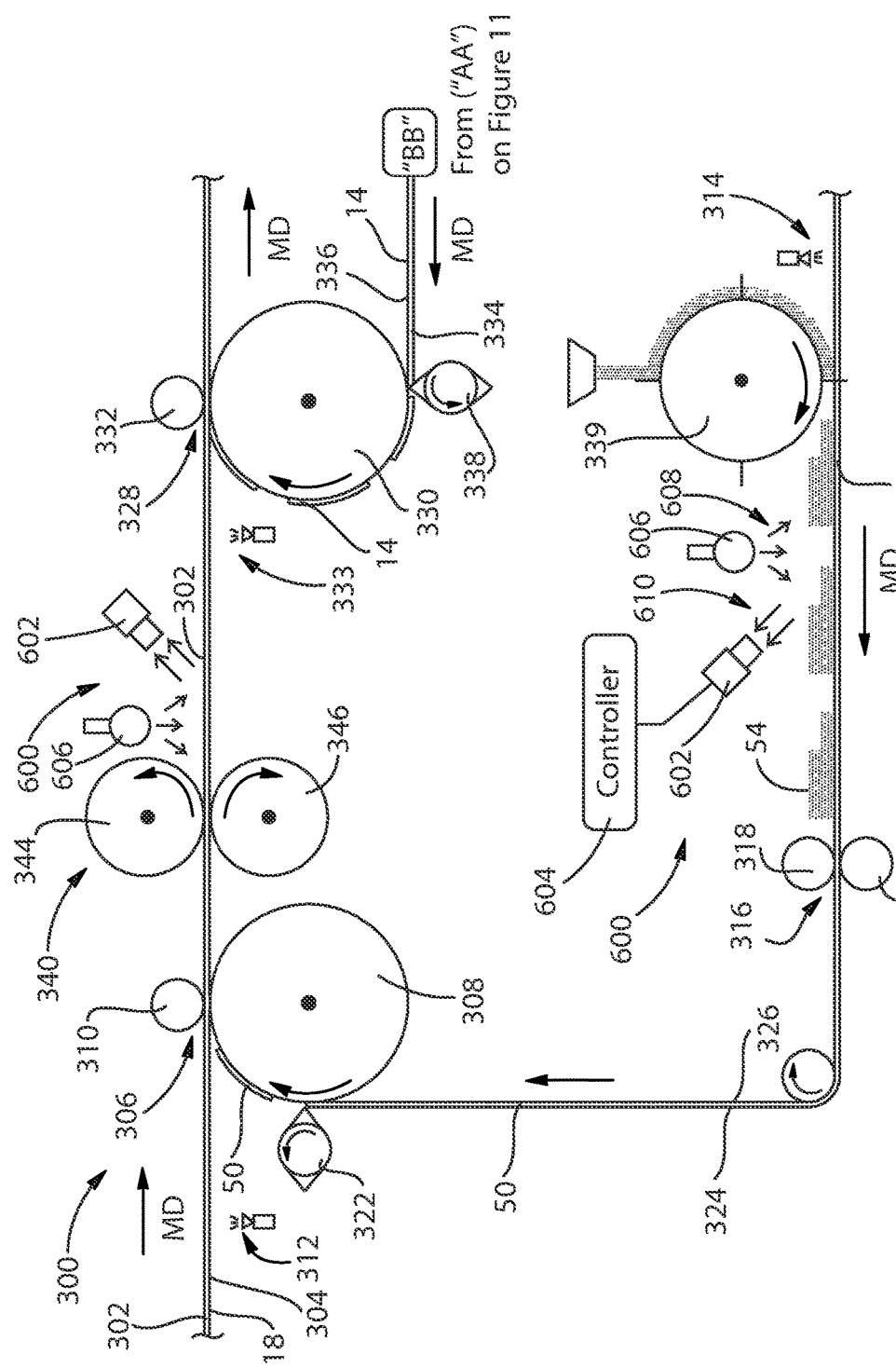
FIG. 15 is a detailed schematic side view of a continuous length of acquisition layers from FIG. 14.
Figure 16:
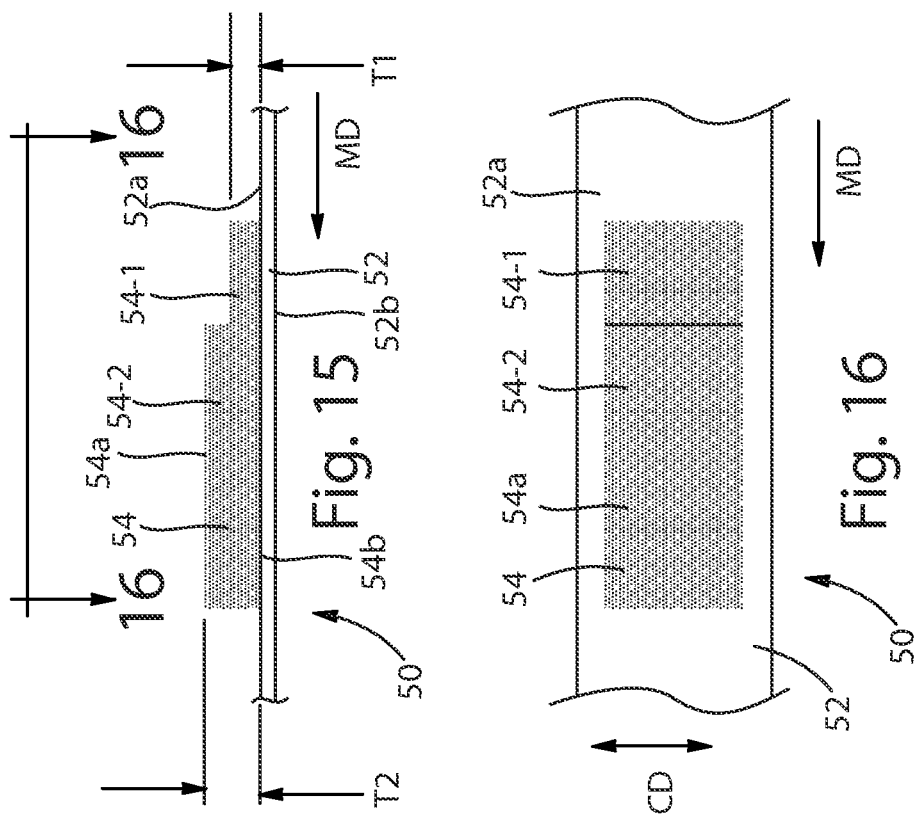
FIG. 16 is a top side view of the continuous length of acquisition layers taken along the sectional line 16-16 of FIG. 15.

It is to be appreciated that the liquid acquisition layer 50 may be formed in various ways before being combined with the topsheet web 18. As discussed above, the liquid acquisition layer 50 may include one or more layers of material. For example, as shown in FIGS. 14-16, the liquid acquisition layer 50 may include a first acquisition layer 52 and a second acquisition layer 54. During assembly, adhesive 314 may applied to the first acquisition layer 52 advancing in a machine direction MD. And discrete patches of second acquisition layers 54 may be assembled on a forming drum 339 and deposited on a continuous length of a first acquisition layer substrate 52 advancing in a machine direction MD. As shown in FIGS. 14-16, each discrete patch of second acquisition layer 54 may comprise two or more regions having different thicknesses extending in the cross direction and the machine direction. For example, the each discrete patch of second acquisition layer 54 may include a first region 54-1 and a second region 54-2, wherein the first region 54-1 defines a first thickness T1 and the second region 54-2 defines a second thickness T2. In some embodiments, the second thickness T2 may be greater than the first thickness T1.

With continued reference to FIGS. 14-16, the first acquisition layer substrate 52 includes a first surface 52a and an opposing second surface 52b, and defines a width in a cross direction CD. And the discrete patches of second acquisition layers 54 each include a first surface 54a and an opposing second surface 54b, and define a width in a cross direction CD. As such, the second surface 54b of each discrete patch 54 may be in a facing relationship with the first surface 52a of the continuous length of the first acquisition layer substrate 52 to form a liquid acquisition layer 50 having a first surface 324 and an opposing second surface 326. The liquid acquisition layer may also advance through a nip 316 between rolls 318, 320 before advancing to the carrier apparatus 308. As shown in FIG. 14, the first acquisition layer substrate 52 may be cut into discrete lengths or patches by a knife roll 322 on the carrier apparatus 308 to form discrete lengths of acquisition layers 50 before being combined with the topsheet web 18.

The carrier apparatus 308 and the knife roll 322 may utilize a cut and slip technique to space sequential discrete lengths of the acquisition layer 50 about the carrier apparatus 308. A cut and slip technique is an operation for achieving spacing between discrete components. An example operation for achieving spacing between discrete components is disclosed in U.S. Pat. No. 5,702,551, which is incorporated by reference herein. Other types of operations and equipment that may be used to cut and space discrete lengths of components are disclosed in U.S. Pat. Nos. 6,620,276; 6,811,019; and 7,587,966, which are incorporated by reference. The discrete lengths of acquisition layer 50 are then combined with the topsheet web 18 at nip 306. In particular, the first surface 324 of the acquisition layer 50 may be adhered to the second surface 304 of the topsheet web 18 at nip 306, and as such, the first acquisition layer 52 may be positioned between the topsheet web 18 and the second acquisition layer 54. Although the acquisition layer 50 is shown in FIG. 14 as being cut into discrete lengths before being combined with the topsheet web 18, it is to be appreciated that in some embodiments a continuous length of acquisition layer 50 may be combined with the topsheet web 18. From the nip 306, the combined topsheet web 18 and liquid acquisition layer 50 advance in the machine direction MD to a nip 328 defined between a carrier apparatus 330 and roll 332, where the topsheet web 18 and acquisition layer are combined with an absorbent core 14. Before entering the nip 328, adhesive 333 may be applied to the second surface 304 of the acquisition layer 50 and/or topsheet web 18.

It is to be appreciated that the absorbent core 14 may be formed in various ways before being combined with the topsheet web 18 and acquisition layer 50. For example, as shown in FIG. 14, the absorbent core 14 has a first surface 334 and an opposing second surface 336 and may be formed in accordance with the process description provided above with reference to FIGS. 1-13. As such, the absorbent core may include various components discussed above with reference to FIGS. 1-8, such as a first absorbent layer 60 and a second absorbent layer 62, wherein the first absorbent layer 60 of the absorbent core 14 may include a substrate 64, an absorbent particular polymer material 66 on the substrate 64, and a thermoplastic composition 68 on the absorbent particulate polymer material 66. And the second absorbent layer 62 of the absorbent core 14 may include a substrate 72, an absorbent particulate polymer material 74 on the second substrate 72, and a thermoplastic composition 66 on the absorbent particulate polymer material 74. As such, with reference to FIGS. 2 and 14, the substrate 72 may define the first surface 334 of the absorbent core 14, and the substrate 64 may define the second surface 336 of the absorbent core 14. As shown in FIG. 14, the absorbent core 14 may also be cut into discrete lengths by a knife roll 338 on the carrier apparatus 330 before being combined with the acquisition layer 50 and topsheet web 18.

The carrier apparatus 330 and the knife roll 338 may also utilize a cut and slip technique to space sequential discrete lengths of the absorbent core 14 about the carrier apparatus 330. A cut and slip technique is an operation for achieving spacing between discrete components. An example operation for achieving spacing between discrete components is disclosed in U.S. Pat. No. 5,702,551, which is incorporated by reference herein. Other types of operations and equipment that may be used to cut and space discrete lengths of components are disclosed in U.S. Pat. Nos. 6,620,276; 6,811,019; and 7,587,966, which are incorporated by reference herein. The discrete lengths of absorbent core 14 are then combined with the acquisition layer 50 and topsheet web 18 at nip 328. In particular, the first surface 334 of the absorbent core 14 may be adhered to the second surface 326 of the acquisition layer 50 at nip 328. Although the absorbent core 14 is shown in FIG. 14 as being cut into discrete lengths before being combined with the acquisition layer 50 and topsheet web 18, it is to be appreciated that in some embodiments a continuous length of absorbent core 14 may be combined with the acquisition layer 50 and topsheet web 18.

From the nip 328, the combined topsheet web 18, acquisition layer 50, and absorbent core 14 advance in the machine direction MD to additional converting operations that complete assembly of the diapers 10. For example, it is to be appreciated that the topsheet web 18, acquisition layer 50, and absorbent core 14 can be combined with other absorbent article components as described above, such as for example, a backsheet, fastening components, leg cuffs, and elasticated features.

As shown in FIGS. 11, 14, and 17-20, an inspection system 600 may be configured to interact with, monitor, and/or control the converting line 300. In some configurations, sensors 602 may be arranged adjacent the converting line 300 and may communicate with a controller 604. Based on such communications, the controller 604 may monitor and affect various operations on the converting line 300. For example, the controller may send various types of control commands to the converter line based on communications with the sensors 602. In some embodiments, the control commands may be in the form of reject commands communicated to a reject system.

It is to be appreciated that the controller 604 may include one or more computer systems. The computer system may, for example, include one or more types of programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators. Process and product data may be stored directly in the controller or may be located in a separate data historian. In some embodiments, the historian is a simple data table in the controller, In other embodiments, the historian may be a relational or simple database. Common historian applications include Rockwell Automation Factory Talk Historian, General Electric Proficy Historian, OSI PI, or any custom historian that may be configured from Oracle, SQL or any of a number of database applications. It is also to be appreciated that various types of controllers and inspection sensors can be configured in various ways and with various algorithms to provide various types of data and perform various functions, for example, such as disclosed in U.S. Pat. Nos. 5,286,543; 5,359,525; 6,801,828; 6,820,022; 7,123,981; 8,145,343; 8,145,344; and 8,244,393; and European Patent No. EP 1528907B1, all of which are incorporated by reference herein.

In some embodiments, the inspection sensors 602 may be configured to create profiles representing surface topographies of absorbent structures. For example, as shown in FIGS. 11, 14, and 17-20, the inspection system 600 may include a radiation source 606 that illuminates a surface of an absorbent structure with a predetermined pattern of light 608 extending in the cross direction CD. Example radiation sources 606 may include a laser line generator, such as for example a Coherent model SNF-501L-660-35-30-K, 660 nm/35 mW. It is to be appreciated that the radiation source 606 and the sensor 602 may be separate stand-alone units or may be incorporated together into another unit, such as for example, a Keyence LJ-V7000 series including a LJ-V7080 head with a LJ-V7001 controller. Such radiation sources may illuminate absorbent structures with light having various wavelengths wherein the light is detectable by the sensor. For example, in some embodiments, a radiation source 606 may illuminate with blue light that can be defined as light having wavelengths from about 370 nm to about 500 nm inclusive. In some embodiments, a radiation source 606 may illuminate with red light that can be defined as light having wavelengths from about 632 nm to about 780 nm inclusive. Example radiation sources 606 may also include a digital light projector or DLP, such as for example, a Light Commander available from Texas Instruments, which may illuminate with white light. In turn, the sensor 602 senses distortions in patterns of light 610 reflected from the illuminated surface of the absorbent structure and triangulates changes in elevation of the illuminated surface of the absorbent structure relative to the sensor 602. In some instances, the sensor 602 may read the position and deformation of a laser line and computes three-dimensional profile at speeds up to 4,000 images per second or 4 KHz. In some embodiments, the sensor 602 may read the position and deformation of a laser line and computes three-dimensional profile at speeds up to 64,000 images per second or 64 KHz. Based on the triangulated changes in elevation, the sensors 602 create a profile representing a surface topography of the illuminated surface of the absorbent structure. It is to be appreciated that various types of sensors 602 may be used, such as for example, structured light sensors. Examples of such sensors may include a Keyence LJ-V7300; Cognex DS1000; SICK Ranger C; and Automation Technology C2-2040HS-GigE. Additional examples of sensors 602 and radiation sources 606 and methods of operation are described in U.S. Pat. Nos. 7,460,250; 7,489,410; and 7,667,857, which are all incorporated herein by reference.

Figure 17:
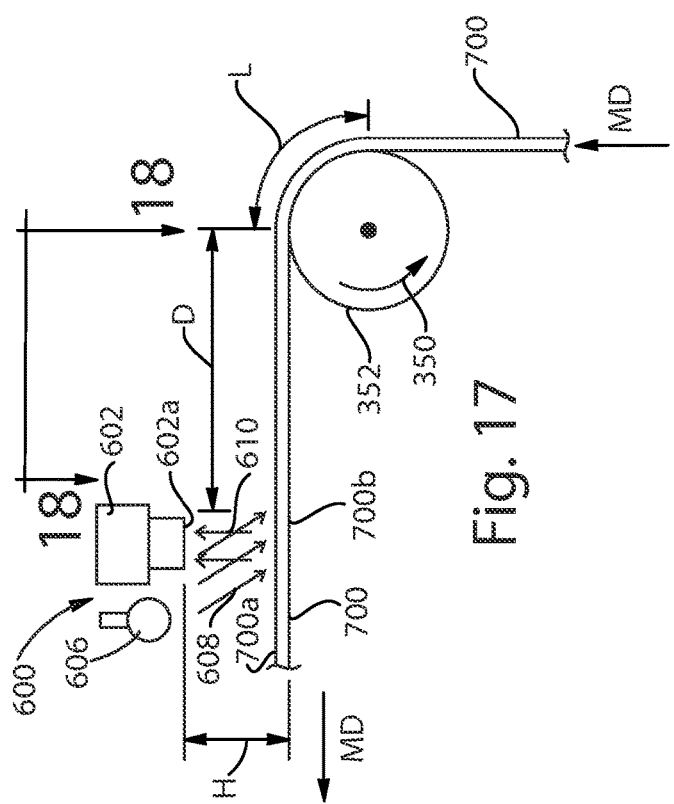
FIG. 17 is a schematic side view of an inspection system with a sensor adjacent an advancing absorbent structure.
Figure 18:
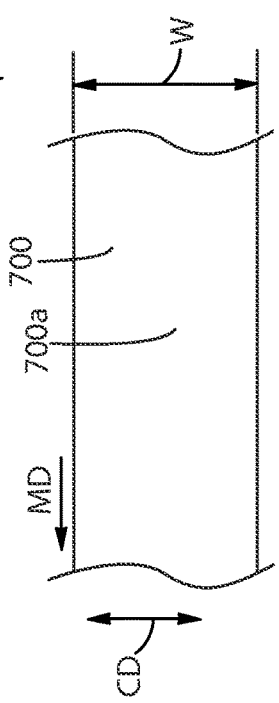
FIG. 18 is a top side view of the advancing absorbent structure taken along the sectional line 18-18 of FIG. 17.

It is to be appreciated that the sensor 602 and/or radiation source 606 may be configured and arranged in various ways relative to advancing substrates or laminates that are being monitored. For example, FIGS. 17 and 18 show an absorbent structure 700 advancing in a machine direction MD adjacent a sensor 602 and radiation source 606. The absorbent structure 700 includes a first surface 700a and an opposing second surface 700b, and defines a width W in a cross direction CD. As shown in FIG. 17, the absorbent structure 700 advances in a machine direction MD onto a support surface 352. The second surface 700b of the absorbent structure 700 may also contact a length L of the support surface 352. And from the support surface 352, the absorbent structure advances 700 in the machine direction MD past the sensor 602. It is to be appreciated that the support surface 352 may be configured in various ways. For example, as shown in FIG. 17, the support surface 352 may be configured as an outer circumferential surface of a rotating drum 350. In other examples, the support surface 352 may be configured as a surface of a stationary bar or a conveyor belt.

With continued reference to FIG. 17, a portion of the first surface 700a of the absorbent structure 700 is illuminated with a predetermined pattern of light 608 extending in the cross direction CD. And the sensor 602 may include a lens 602a adapted to receive light 610 reflected from the absorbent structure 700. As previously mentioned, the sensor 602 senses distortions in patterns of light 610 reflected from the illuminated surface 700a of the absorbent structure 700 and triangulates changes in elevation of the illuminated surface 700a of the absorbent structure relative 700 to the sensor 602. As shown in FIG. 17, the lens 602a of the sensor 602 may be positioned a distance D along the machine direction MD from the support surface 352 to where the first surface 700a of the absorbent structure 700 is illuminated with the predetermined pattern of light 608. Thus, the first surface 700a of the absorbent structure advances a distance D from the support surface 352 to where the first surface 700a of the absorbent structure 700 is illuminated with the predetermined pattern of light 608. As such, the first surface 700a of the absorbent structure 700 is positioned between the lens 602a of the sensor 602 and the second surface 700b. The sensor 602 may also be positioned relative to the absorbent structure 700 so as to define a distance H between second surface 700b of the absorbent structure 700 and the lens 602a.

Figure 19:
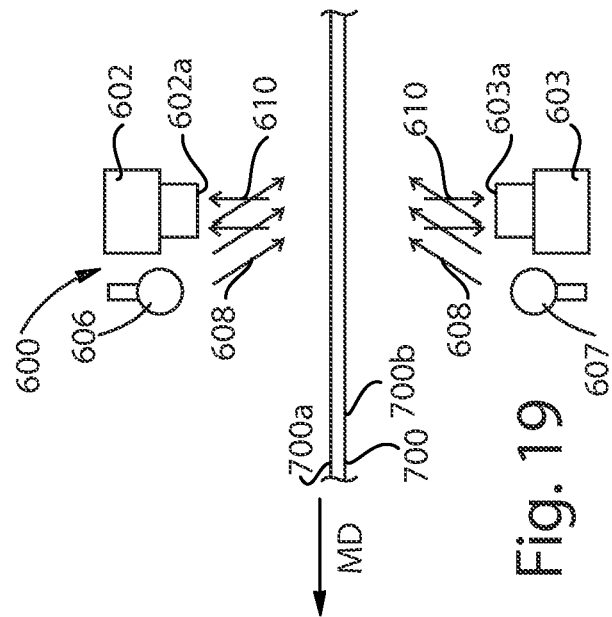
FIG. 19 is a schematic side view of an inspection system including sensors arranged on opposing sides of an advancing absorbent structure.

It is to be appreciated that the sensor 602 and/or radiation source 606 may be located in various positions relative to the absorbent structure 700. For example, with continued reference to FIGS. 17 and 18, the sensor 602, radiation source 606, absorbent structure 700, and support surface 352 may be positioned such that the ratio of the distance D to the width W of the absorbent structure 700 is about 10:1 or less. In some embodiments, the ratio of the distance D to the width W is about 3:1 or less. In some embodiments, the ratio of the distance D to the length L is about 5:1 or less. In some embodiments, the ratio of the distance D to the length L is about 3:1 or less. It is to be appreciated that the inspection systems 600 may include more than one sensor and/or radiation source positioned to monitor the same or opposing sides of an advancing absorbent structure. For example, as shown in FIG. 19, the inspection system 600 includes a first sensor 602 and a first radiation source 606 adjacent the first surface 700a of the advancing absorbent structure 700. In addition, the inspection system 600 includes a second sensor 603 and a second radiation source 607 adjacent the second surface 700b of the advancing absorbent structure 700.

Figure 20:
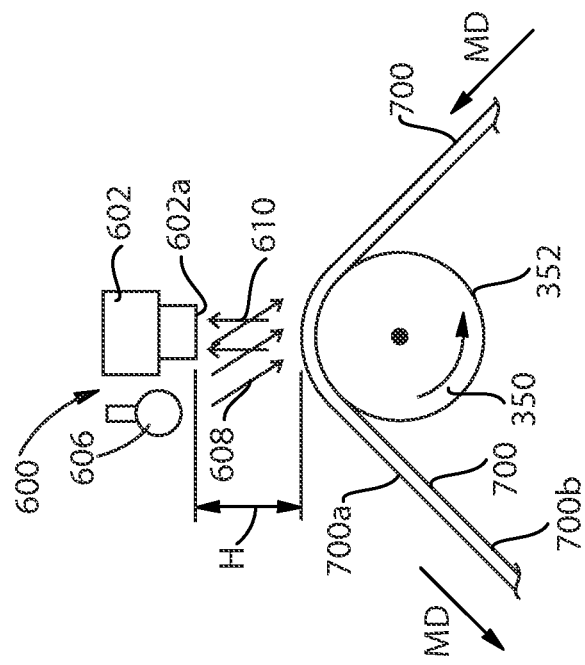
FIG. 20 is a schematic side view of an inspection system with a sensor adjacent an advancing absorbent structure on a support surface.

In other arrangements, the sensor 602 may be located adjacent the absorbent structure 700 in a position where the absorbent structure is in contact with the support surface 352. For example, as shown in FIG. 20, the inspection system 600 may includes a sensor 602 and a radiation source 606 adjacent the first surface 700a of the advancing absorbent structure 700 at a position wherein the absorbent structure is in contact with the support surface 352. As such, the sensor 602 may also be positioned relative to the absorbent structure 700 so as to define a distance H between support surface 352 and the lens 602a.

It is to be appreciated that the absorbent structure 700 shown in FIGS. 17-20 provides a generic representation of a substrate and/or laminates discussed above. Thus, it should be appreciated, for example, that the absorbent structure 700 shown in FIGS. 17-20 may be equated with the continuous lengths of absorbent cores 14 discussed above. As such, the first surface 700a or the second surface 700b of the absorbent structure 700 may be equated with the second surface 72b of the second continuous substrate 72 or the second surface 64b of the first continuous substrate 64 of the continuous lengths of absorbent cores 14, such as shown for example in FIGS. 11 and 14. In another example, the absorbent structure 700 shown in FIGS. 17 and 18 may be equated with the continuous lengths of acquisition layers 50 discussed above. As such, the first surface 700a or the second surface 700b of the absorbent structure 700 may be equated with the first surface 54a of the second acquisition layer 54 and/or the first surface 52a of the first acquisition layer 52, such as shown for example in FIGS. 14-16. In yet another example, the first surface 700a or the second surface 700b shown in FIGS. 17-20 may be equated with the first surface 302 or the second surface 304 of the continuous topsheet web 18 shown in FIGS. 14 and 14A.

With reference to FIGS. 9-14 and 17-20, the inspection system 600 may be configured to illuminate the second surface 72b of the second continuous substrate 72 of the continuous length of substantially cellulose free absorbent cores 14 with a predetermined pattern of light 608 extending in the cross direction CD. Distortions in patterns of the light 610 reflected from the second surface 72b of the second continuous substrate 72 may be sensed with the sensor 602 to triangulate changes in elevation of the second surface 72b of the second continuous substrate 72 relative to the sensor 602. As such, the inspection system 600 may create a profile representing a surface topography of channel regions 115 in the continuous length of substantially cellulose free absorbent cores 14 from the triangulated changes in elevation. In turn, the inspection system 600 may determine a characteristic of a channel region 115 based on the profile. Such a characteristic may include, for example, a presence absorbent particulate polymer material in the channel region, a shape of the channel region, an orientation of the channel region, and/or a position of the channel region.

With reference to FIGS. 15-20, the inspection system 600 may be configured to illuminate the first surfaces 54a of the discrete patches of second acquisition layers 54 with a predetermined pattern of light 608 extending in the cross direction CD. Distortions in patterns of the light 610 reflected from the first surfaces 54a of the discrete patches of second acquisition layers 54 may be sensed with the sensor 602 to triangulate changes in elevation of the first surfaces 54a of the discrete patches of second acquisition layers 54. As such, the inspection system 600 may create a profile representing a surface topography of discrete patches of second acquisition layers 54 from the triangulated changes in elevation. In turn, the inspection system 600 may determine a characteristic of a discrete patch of second acquisition layer 54 based on the profile. Such a characteristic may include for example, the first thickness T1 and/or the second thickness T2.

Although the methods and apparatuses herein have been presented and described in the context of creating profiles representing surface topographies of absorbent structures, such as acquisition layers and absorbent cores, it is to be to be appreciated that the methods and apparatuses herein may be applied to other absorbent article components at various stages of manufacture. As such, inspections systems utilizing sensors and radiation sources as described above may be configured and positioned adjacent to converting apparatuses to create profiles representing surface topographies of such absorbent article components.

In some configurations, embossing processes may be applied to various components of absorbent articles during manufacture, such as disclosed in U.S. Pat. Nos. 6,563,013; 8,603,277; and 8,658,852 as well as U.S. Patent Publication No. US2006/0116653A1, which are all incorporated by reference herein. In turn, inspections systems utilizing sensors and radiation sources as described above may be configured and positioned adjacent to converting apparatuses to create profiles representing surface topographies of such embossed absorbent article components. For example, as shown in FIG. 14, the combined topsheet web 18, acquisition layer 50, and absorbent core 14 advance from the nip 328 in the machine direction MD to an embossing apparatus 340, where a pattern is embossed into the topsheet web 18. The embossing apparatus may include an embossing nip 342 defined between a patterned embossing roll 344 and an anvil roll 346. As shown in FIG. 14, the combined topsheet web 18, acquisition layer 50, and absorbent core 14 advance in the machine direction MD through the embossing nip 342 such that the outer surface of the patterned embossing roll 344 engages the first surface 302 of the topsheet web and the outer surface of the anvil roll engages the second surface 336 of the absorbent core 14. The topsheet web 18, acquisition layer 50, and absorbent core 14 are compressed while advancing through the embossing nip 342, and the embossing roll 344 embosses a pattern of embossments into the topsheet web 18. It is to be appreciated that the topsheet web 18, acquisition layer 50, and absorbent core 14 can be combined with other absorbent article components as described above in an assembly process, such as for example, a backsheet, fastening components, leg cuffs, and elasticated features. As such, an inspection system 600 utilizing sensors 602 and radiation sources 606 described above may be configured and positioned downstream of the embossing apparatus 340 adjacent the embossed components to create profiles representing surface topographies of embossed topsheet web 18 in combination with acquisition layers 50 and/or absorbent cores 14.

Building on the above discussion, it is to be appreciated the embossing processes may be carried out in various stages of the assembly process. For example, as shown in FIG. 14A, the embossing apparatus 340 is positioned upstream of the nip 328. As such, the combined topsheet web 18 and acquisition layer 50 advance from the nip 306 in the machine direction MD to the embossing apparatus 340, where a pattern is embossed into the topsheet web 18. The embossing apparatus may include an embossing nip 342 defined between a patterned embossing roll 344 and an anvil roll 346. As shown in FIG. 14A, the combined topsheet web 18 and acquisition layer 50 advance in the machine direction MD through the embossing nip 342 such that the outer surface of the patterned embossing roll 344 engages the first surface 302 of the topsheet web and the outer surface of the anvil roll engages the second surface 326 of the acquisition layer 50. The topsheet web 18 and acquisition layer 50 are compressed while advancing through the embossing nip 342, and the embossing roll 344 embosses a pattern of embossments into the topsheet web 18. From the embossing apparatus 340, the combined topsheet web 18 and acquisition layer 50 may then advance in the machine direction MD to the nip 328 defined between a carrier apparatus 330 and roll 332, where the topsheet web 18 and acquisition layer are combined with an absorbent core 14. Before entering the nip 328, adhesive 333 may be applied to the second surface 304 of the acquisition layer 50 and/or topsheet web 18. As such, an inspection system 600 utilizing sensors 602 and radiation sources 606 described above may be configured and positioned downstream of the embossing apparatus 340 adjacent the embossed components to create profiles representing surface topographies of embossed topsheet web 18 in combination with the acquisition layers 50.

In yet other configurations, inspections systems utilizing sensors and radiation sources as described above may be configured and positioned adjacent to converting apparatuses to create profiles representing surface topographies of bonds on absorbent article components. For example, the methods and apparatuses herein may be configured to create profiles representing surface topographies of bonds and/or seams created with pressure, heat, and/or ultrasonic bonding processes, such as disclosed in U.S. Pat. Nos. 4,919,738; 6,248,195; and 7,108,759; U.S. Patent Publication Nos. US2013/0213547 A1 and US2013/0218116 A1; and U.S. Patent Application Nos. 61/836,745; 61/836,690; Ser. No. 14/038,812; Ser. No. 14/135,687, which are all incorporated herein by reference.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling disposable absorbent articles, each absorbent article comprising a topsheet, a backsheet, and a substantially cellulose free absorbent core disposed between the topsheet and the backsheet, the method comprising the steps of:
   advancing a first continuous substrate in a machine direction, the first continuous substrate having a first surface and an opposing second surface, and defining a width in a cross direction;
   depositing absorbent particulate polymer material on the first surface of the first continuous substrate so as to define first regions of absorbent particulate polymer material surrounding second regions that are substantially free of absorbent particulate polymer material;
   advancing a second continuous substrate in the machine direction, the second continuous substrate having a first surface and an opposing second surface, and defining a width in the cross direction;
   depositing absorbent particulate polymer material on the first surface of the second continuous substrate so as to define first regions of absorbent particulate polymer material surrounding second regions that are substantially free of absorbent particulate polymer material;
   combining the first continuous substrate with the second continuous substrate to create a continuous length of substantially cellulose free absorbent cores, wherein the second regions on the first continuous substrate and the second continuous substrate are placed in facing relationships to define channel regions having a first thickness T1 surrounded by absorbent particulate polymer material areas having a second thickness T2, wherein first thickness T1 is less than the second thickness T2;

advancing the continuous length of substantially cellulose free absorbent cores past a sensor such that the second continuous substrate is between the sensor and the first continuous substrate;

illuminating the second surface of the advancing second continuous substrate of the continuous length of substantially cellulose free absorbent cores with a predetermined pattern of light extending in the cross direction;

sensing distortions in patterns of light reflected from the second surface of the advancing second continuous substrate with the sensor to triangulate changes in elevation of the second surface of the second continuous substrate relative to the sensor; and creating a profile representing a surface topography of channel regions in the continuous length of substantially cellulose free absorbent cores from the triangulated changes in elevation.

2. The method of claim 1, further comprising the step of: determining a characteristic of a channel region based on the profile, the at least one characteristic selected from the group consisting of: a presence absorbent particulate polymer material in the channel region, a shape of the channel region, and position of the channel region.

3. The method of claim 1, further comprising advancing the second surface of the first continuous substrate on a support surface.

4. The method of claim 3, wherein the support surface comprises an outer circumferential surface of a rotating drum.

5. The method of claim 3, wherein a lens of the sensor is positioned a distance H from the second surface of the first continuous substrate; and wherein the lens of the sensor is positioned the distance H from the support surface.

6. The method of claim 3, wherein the continuous length of substantially cellulose free absorbent cores defines a width W in the cross direction, wherein the second continuous substrate advances a distance D from the support surface to where the second surface of the second continuous substrate of the continuous length of substantially cellulose free absorbent cores is illuminated with the predetermined pattern of light, and wherein the ratio of the distance D to the width W is about 10:1 or less.

7. The method of claim 6, wherein the ratio of the distance D to the width W is about 3:1 or less.

8. The method of claim 3, the second surface of the first continuous substrate contacts a length L of support surface, and wherein the second continuous substrate advances a distance D from the support surface to where the second surface of the second continuous substrate of the continuous length of substantially cellulose free absorbent cores is illuminated with the predetermined pattern of light, and wherein the ratio of the distance D to the length L is about 5:1 or less.

9. The method of claim 8, wherein the ratio of the distance D to the length L is about 3:1 or less.

10. The method of claim 1, further comprising the steps of:
advancing the continuous length of substantially cellulose free absorbent cores past a second sensor such that the first continuous substrate is between the second sensor and the second continuous substrate;
illuminating the second surface of the first continuous substrate of the continuous length of substantially cellulose free absorbent cores with a predetermined pattern of light extending in the cross direction; and
sensing distortions in patterns of the light reflected from the second surface of the first continuous substrate to triangulate changes in elevation of the second surface of the first continuous substrate relative to the second sensor.

11. The method of claim 10, wherein the step of creating the profile representing the surface topography of channel regions in the continuous length of substantially cellulose free absorbent cores is further based on the triangulated changes in elevation of the second surface of the first continuous substrate relative to the second sensor.

12. The method of claim 1, wherein the step of illuminating further comprises illuminating with a radiation source, wherein the radiation source is not a laser.

13. A method for assembling disposable absorbent articles, each absorbent article comprising a topsheet, a backsheet, and a liquid acquisition layer and an absorbent core disposed between the topsheet and the backsheet, the method comprising the steps of:

advancing a continuous length of a first acquisition layer substrate in a machine direction the first continuous length of the first acquisition layer substrate having a first surface and an opposing second surface, and defining a width in a cross direction;

depositing discrete patches of second acquisition layers on the continuous length of the first acquisition layer substrate, wherein each discrete patch includes a first surface and an opposing second surface, wherein the second surface of each discrete patch is in a facing relationship with the first surface of the continuous length of the first acquisition layer substrate;

advancing the continuous length of the first acquisition layer substrate past a sensor such that discrete patches of second acquisition layers advance between the sensor and the continuous length of the first acquisition layer substrate;

illuminating the first surfaces of the advancing discrete patches of second acquisition layers with a predetermined pattern of light extending in the cross direction;

sensing distortions in patterns of the light reflected from the first surfaces of the advancing discrete patches of second acquisition layers with the sensor to triangulate changes in elevation of the first surfaces of the discrete patches of second acquisition layers; and creating a profile representing a surface topography of discrete patches of second acquisition layers from the triangulated changes in elevation.

14. The method of claim 13, wherein each discrete patches of second acquisition layer comprises regions extending in the cross direction and the machine direction, wherein a first region defines a first thickness T1, and a second region defines a second thickness T2, and wherein T2>T1.

15. The method of claim 14, further comprising the step of: determining a characteristic of a discrete patch of second acquisition layer based on the profile, the at least one characteristic selected from the group consisting of: the first thickness T1 and the second thickness T2.

16. The method of claim 14, further comprising the step of: cutting the continuous length of a first acquisition layer substrate to create discrete liquid acquisition layers each comprising a discrete patch of first acquisition layer and a discrete patch of second acquisition layer.

17. The method of claim 16, further comprising the steps of:
advancing a continuous topsheet web; and
combining discrete liquid acquisition layers with the continuous topsheet web, wherein discrete patches of first acquisition layer are positioned between the continuous topsheet web and discrete patches of second acquisition layer.

18. The method of claim 17, further comprising the step of:
combining absorbent cores with the continuous topsheet web, wherein liquid acquisition layers are positioned between absorbent cores and the continuous topsheet web.

19. The method of claim 18, wherein the absorbent cores are substantially cellulose free absorbent cores.

20. A method for assembling disposable absorbent articles, each absorbent article comprising a topsheet, a backsheet, and a liquid acquisition layer and an absorbent core disposed between the topsheet and the backsheet, the method comprising the steps of:
advancing a topsheet web in machine direction, the topsheet web having a first surface and an opposing second surface, and defining a width in a cross direction;
combining a liquid acquisition layer with the topsheet web, wherein the liquid acquisition layer includes a first surface and an opposing second surface, and wherein the first surface of the liquid acquisition layer is positioned in a facing relationship with the second surface of the topsheet web;
providing an embossing nip between a rotating patterned embossing roll and a rotating anvil roll; and
embossing a pattern in the topsheet web by advancing the combined topsheet web and liquid acquisition layer through the embossing nip;
advancing the combined topsheet web and liquid acquisition layer past a sensor;
illuminating at least one of the first surface and the second surface of the advancing topsheet web with a predetermined pattern of light extending in the cross direction;
sensing distortions in patterns of the light reflected from the advancing topsheet web with the sensor to triangulate changes in elevation of the first surface of the topsheet web; and
creating a profile representing a surface topography of first surface of the topsheet web from the triangulated changes in elevation.

21. The method of claim 20, further comprising the step of:
combining an absorbent core with the liquid acquisition layer, wherein the absorbent core includes a first surface and an opposing second surface, and wherein the first surface of the absorbent core is positioned in a facing relationship with the second surface of the liquid acquisition layer.

22. The method of claim 21, wherein the step of combining an absorbent core with the liquid acquisition layer is performed subsequent to the step of embossing a pattern in the topsheet web.

23. The method of claim 21, wherein the step of embossing further comprises advancing the combined topsheet web, liquid acquisition layer, and absorbent core through the embossing nip, wherein the rotating patterned embossing roll contacts the first surface of the topsheet web, and wherein the rotating anvil roll contacts the second surface of the absorbent core.

24. The method of claim 21, wherein the absorbent core is a substantially cellulose free absorbent core.

* * * * *